United States Patent
Odom et al.

(10) Patent No.: US 10,854,911 B2
(45) Date of Patent: Dec. 1, 2020

(54) 1,9,10-SUBSTITUTED PHENOTHIAZINE DERIVATIVES WITH STRAINED RADICAL CATIONS AND USE THEREOF

(71) Applicant: University of Kentucky Research Foundation, Lexington, KY (US)

(72) Inventors: Susan A. Odom, Lexington, KY (US); Chad Risko, Lexington, KY (US); Matthew D. Casselman, Lexington, KY (US); Corrine F. Elliott, Lexington, KY (US); N. Harsha Attanayake, Lexington, KY (US); Subrahmanyam Modekrutti, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/654,464

(22) Filed: Jul. 19, 2017

(65) Prior Publication Data
US 2018/0026297 A1   Jan. 25, 2018

Related U.S. Application Data

(60) Provisional application No. 62/364,060, filed on Jul. 19, 2016.

(51) Int. Cl.
*H01M 10/056* (2010.01)
*C07D 279/22* (2006.01)
(Continued)

(52) U.S. Cl.
CPC ........ *H01M 10/056* (2013.01); *C07D 279/20* (2013.01); *C07D 279/22* (2013.01);
(Continued)

(58) Field of Classification Search
None
See application file for complete search history.

(56) References Cited

U.S. PATENT DOCUMENTS

| | | | |
|---|---|---|---|
| 2008/0296169 A1* | 12/2008 | Davidson | C25B 1/04 205/337 |
| 2017/0062842 A1* | 3/2017 | Huang | C07D 279/22 |
| 2017/0244132 A1* | 8/2017 | Wagner | H01M 10/0525 |

FOREIGN PATENT DOCUMENTS

WO    WO-2016011393 A1 *   1/2016   ........ H01M 10/0525

OTHER PUBLICATIONS

Casselman, et al., Beyond the Hammett Effect: Using Strain to Alter the Landscape of Electrochemical Potentials; ChemPhysChem 2017, 18, 2142-2146.

(Continued)

*Primary Examiner* — Amanda C. Walke
(74) *Attorney, Agent, or Firm* — Stites & Harbison PLLC; Mandy Wilson Decker; Summer Elizabeth Young

(57) ABSTRACT

Compounds for use in a rechargeable battery are provided, including a compound according to the formula:

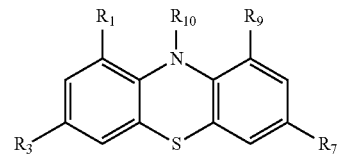

wherein $R_1$ and $R_9$ are independently selected from the group consisting of H, alkyl, aryl, perfluoroaryl, perfluoroalkyl, alkylaryl, alkoxyaryl, alkylcarboxyl, aryl carbonyl, haloalkyl, perfluoroalkyl, glycols, haloaryl, a negative electrolyte, and a polymer, so long as when $R_1$ is H, $R_9$ is not H;

(Continued)

and $R_{10}$ is selected from the group consisting of methyl, alkyl, aryl, alkylaryl, alkoxyaryl, alkylcarboxyl, aryl carbonyl, haloalkyl, perfluoroalkyl, perfluoroaryl, glycols, haloaryl, an oligomer, and a polymer.

21 Claims, 15 Drawing Sheets

(51) Int. Cl.
*C07D 279/20* (2006.01)
*H01M 10/0525* (2010.01)
*H01M 4/133* (2010.01)
*H01M 4/131* (2010.01)
*H01M 8/18* (2006.01)
*H01M 10/0567* (2010.01)
*H01M 4/02* (2006.01)
*H01M 4/587* (2010.01)

(52) U.S. Cl.
CPC ........... *H01M 4/131* (2013.01); *H01M 4/133* (2013.01); *H01M 8/18* (2013.01); *H01M 8/188* (2013.01); *H01M 10/0525* (2013.01); *H01M 10/0567* (2013.01); *H01M 4/587* (2013.01); *H01M 2004/027* (2013.01); *H01M 2004/028* (2013.01); *Y02E 60/50* (2013.01)

(56) References Cited

OTHER PUBLICATIONS

Casselman, et al., Supporting Information Beyond the Hammett Effect: Using Strain to Alter the Landscape of Electrochemical Potentials, pp. 1-17, (2017).

* cited by examiner

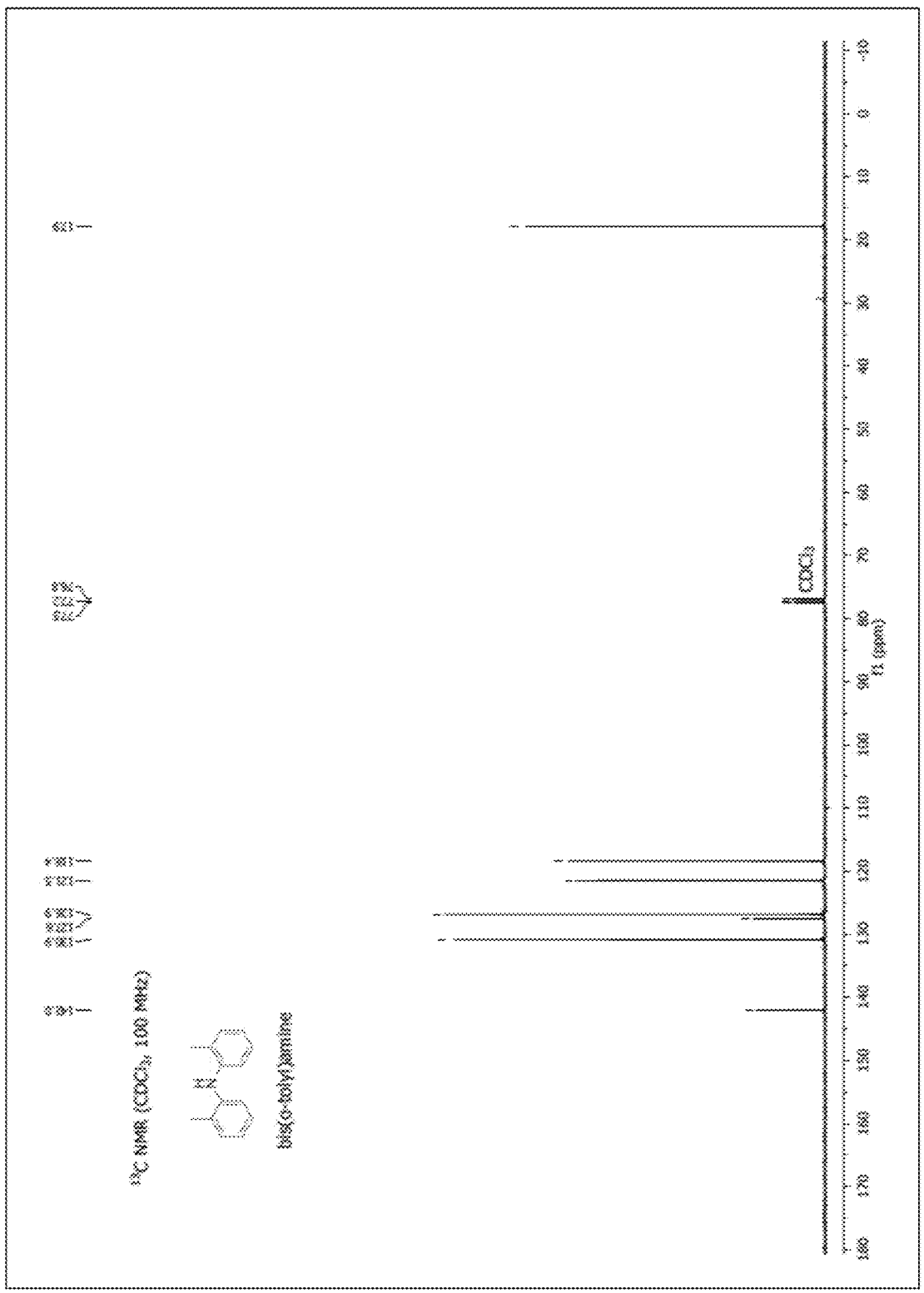
Figure 12a, Con't

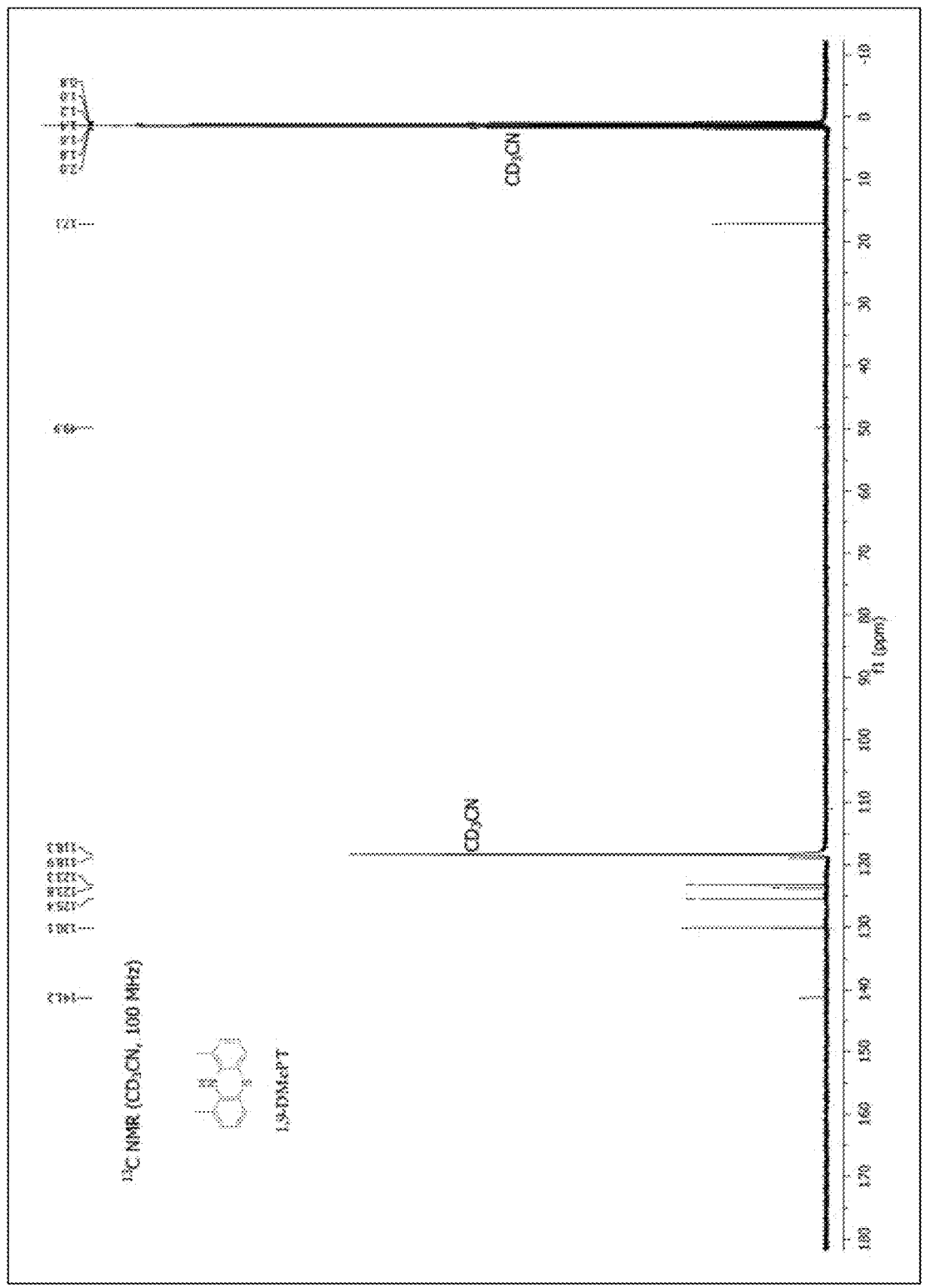
Figure 12b, Con't

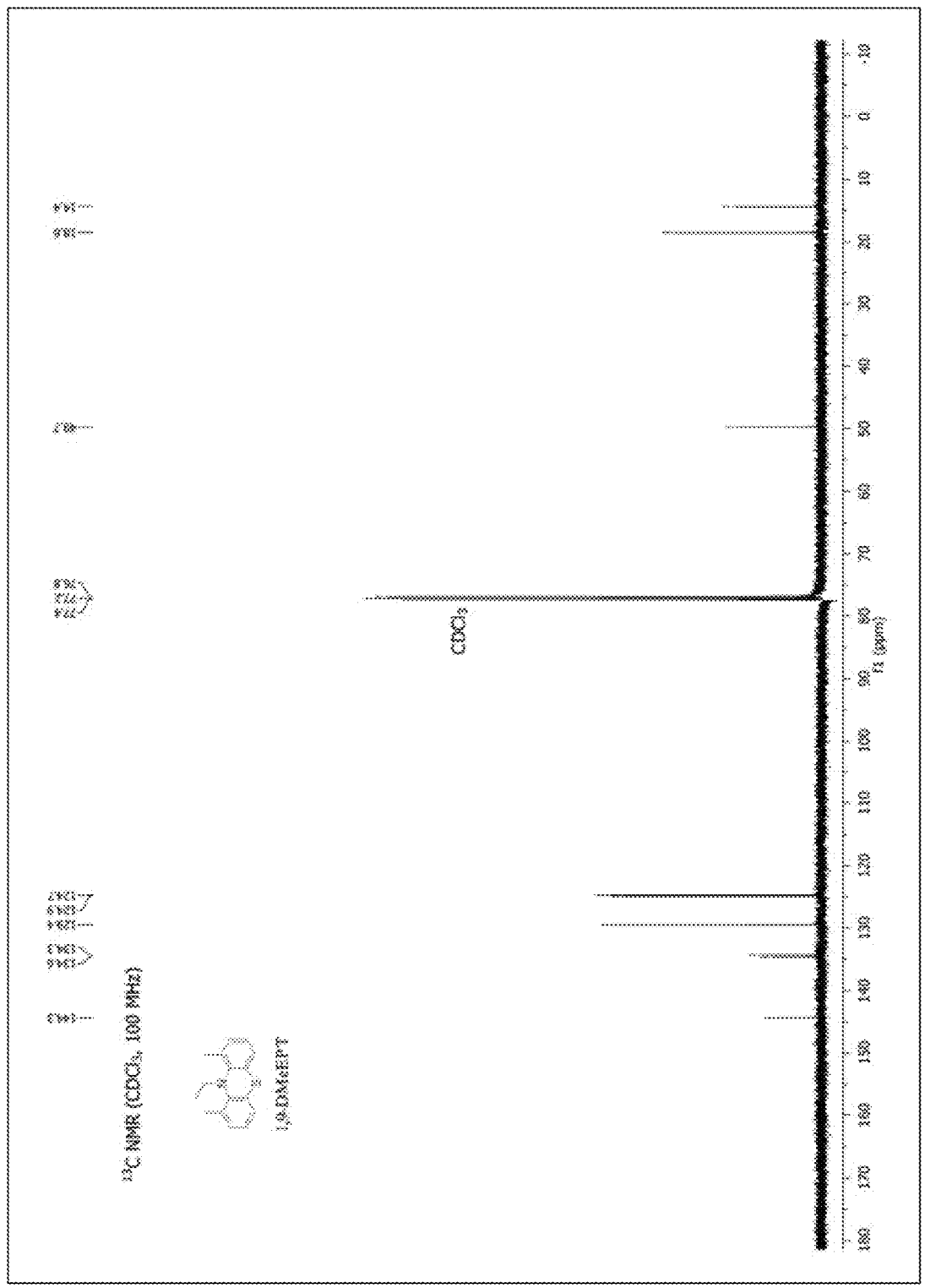
Figure 12c, Con't

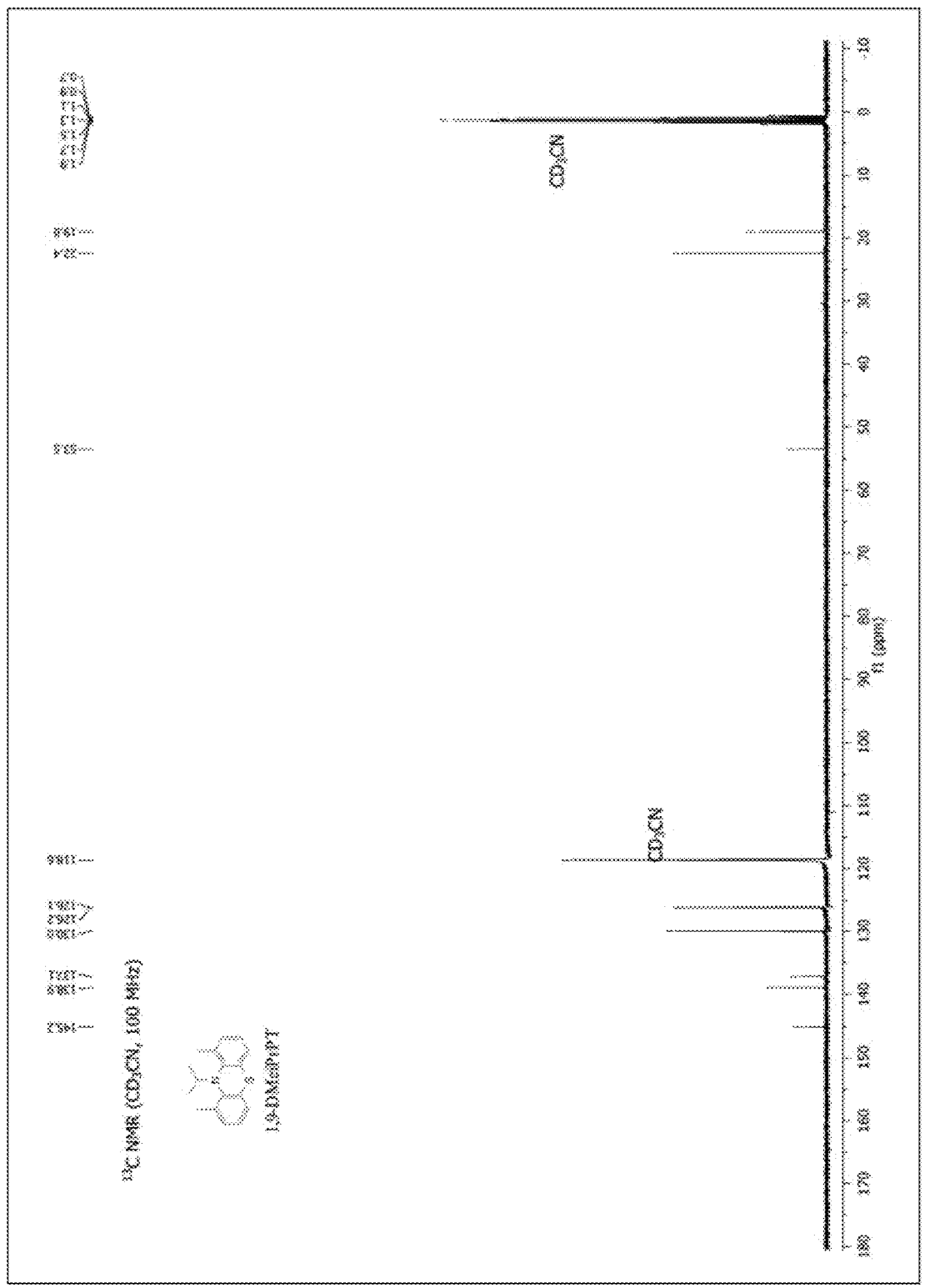
Figure 12d, Con't

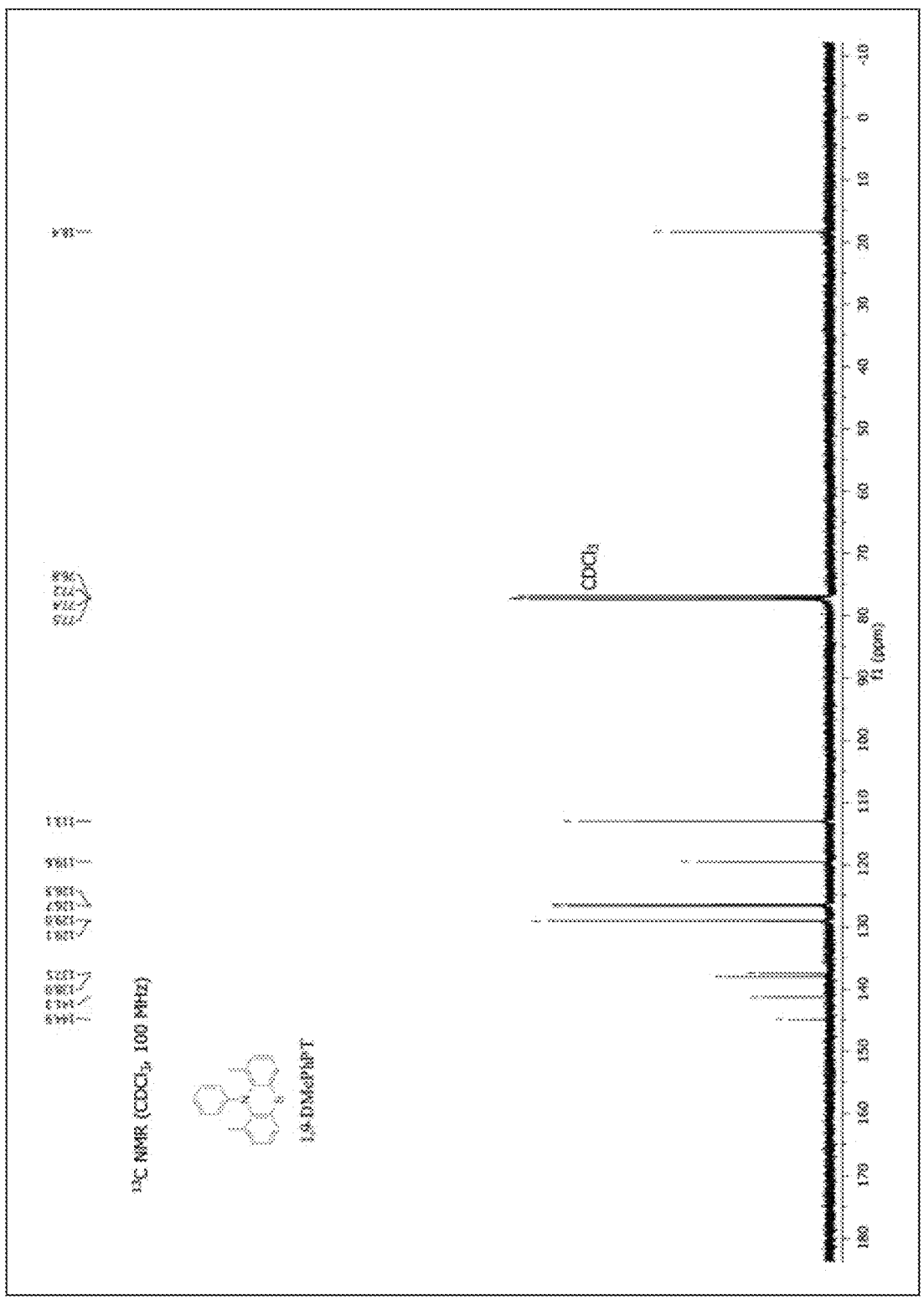
Figure 12e, Con't

1,9,10-SUBSTITUTED PHENOTHIAZINE DERIVATIVES WITH STRAINED RADICAL CATIONS AND USE THEREOF

PRIORITY

This invention claims priority to U.S. Provisional Application Ser. No. 62/364,060 filed Jul. 19, 2016.

GOVERNMENT INTEREST

This invention was made with government support under grant number 1300653 awarded by the National Science Foundation. The government has certain rights in the invention.

TECHNICAL FIELD

The presently-disclosed subject matter generally relates to substituted phenothiazine derivatives that contain substituents at the 1,10 position or at the 1,9,10 position that raise oxidation potentials regardless of whether the substituent is electron-donating or electron withdrawing, without necessarily concomitantly raising reduction potentials.

INTRODUCTION

The redox potentials of π-conjugated organic molecules and polymers are important factors that determine, in part, their performance in organic electronic devices and in energy collection and storage applications. In these systems, the general prescriptions to control redox potentials involve substitution with electron-donating and/or electron-withdrawing groups, making use of the well-known Hammett constants as predictors of the extent of the change of redox potentials,[1] and/or modifying the length of the π-conjugation pathway, e.g. going from ethylene to butadiene to hexatriene and beyond.

Another route to modify molecular redox potentials exploits strain-induced disruptions of the π-conjugated framework) Such chemical modifications typically use so-called bulky substituents to manipulate the dihedral torsions among the π-conjugated moieties that make up the molecular systems. Prime examples include biphenyl (or more generally oligo- or polyphenylenes), where substituents incorporated at the 2, 2', 6, and/or 6' positions increase the twist angle between the phenyl groups, and oligothiophenes, where similar tactics are employed with substituents placed at the 3 and/or 4 positions) Notably, these considerations have been widely used in the development of π-conjugated polymers for electronics and solar cell applications.

Strain has also been used to instill curvature into π-conjugated networks to alter optical and/or redox characteristics, for example in fullerenes,[4] cyclized stilbenes,[5] and twisted acenes (so-called 'twistacenes').[6] In each of these latter examples, the π-conjugated networks are strained in both the ground (neutral) and ionized (oxidized or reduced) electronic states.

Molecular redox shuttles can be used to mitigate excess current in overcharging batteries by spatially ferrying charge through a series of electron-transfer reactions, oxidizing to their radical-cation form at the cathode and reducing to their neutral form at the anode. For molecules designed to mitigate overcharge in LIBs, chemical substitutions are made to adjust the oxidation potentials with respect to the reduction potential of the cathode to ensure that the shuttles become redox active just after a cell is fully charged.[8] Extensive overcharge protection has been demonstrated for lower-voltage $LiFePO_4$ cathodes,[8a,9] which require shuttles that oxidize at potentials of 3.8 to 3.9 V vs. $Li^{+/0}$. However, the protection of higher-voltage cathodes (i.e. $LiCoO_2$, $LiMnO_2$, and $LiNi_{1/3}Mn_{1/3}Co_{1/3}O_2$) require oxidation potentials of 4.2 V or higher, and no shuttle has provided extensive protection in cells containing graphitic anodes.

Maximizing both the energy density and the durability of a LIBs requires charging to a precise voltage: below that potential, the full capacity of the cell is not utilized; at higher potentials, a cell enters overcharge, a condition that can seriously degrade LIBs and lead to hazardous operating conditions.[8]

The road to higher oxidation potential shuttles via the incorporation of strong electron-withdrawing groups on viable low-voltage shuttles can introduce perils in the framework of LIB s. Electron-withdrawing substituents shift both the oxidation and reduction potentials to more positive values, producing compounds that are more susceptible to decomposition through subsequent reactions after reduction to the radical anion at the anode.[7a,10] Premature failure of phenothiazine redox shuttles containing chlorine, bromine, cyano, or nitro groups can be traced back to having reduction potentials >0 V vs. $Li^{+/0[7a,10e]}$ Dimethoxybenzene derivatives containing strongly electron-withdrawing groups have short-lived performance in overcharge when incorporated into lithium-ion cells containing graphite anodes,[10a-d] perhaps as a result of reductive decomposition at the anode/electrolyte interface. This is supported by reports of the redox shuttle 1,4-di-tert-butyl-2,5-bis(2,2,2-trifluoroethoxy)benzene surviving 2× longer in a cells containing the $Li_4Ti_5O_{12}$ anode when compared to LIBs with either the highly reducing graphitic or lithium metal anodes.[10b]

As such, the incorporation of strongly electron-withdrawing groups is a problematic route for molecules that require stability at both high and low redox potentials. Thus, a new approach for designing stable, high-voltage redox shuttles is needed.

SUMMARY

In some embodiments of the subject matter, the phenothiazine derivatives presently disclosed can be used in rechargeable batteries to confer overcharge protection in such batteries. In particular, certain embodiments of the presently-disclosed subject matter relate to conferring overcharge protection in lithium-ion batteries and/or lithium-air batteries and/or redox flow batteries.

In some embodiments of the subject matter, the phenothiazine derivatives can be used as photo-redox catalysts, photoinitiators, redox mediators in electrochemical surface patterning, and in other applications.

Embodiments of compounds disclosed herein are substantially more planar in their radical-cation states as compared to their neutral states. Embodiments of compounds disclosed herein have increased oxidation potentials without requiring use of electron-withdrawing groups, leading to less-easily accessed reduction potentials.

In some embodiments, the phenothiazine compound is provided according to the formula:

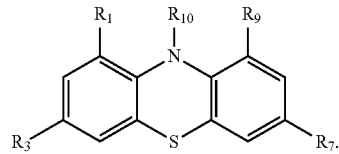

In some embodiments of the formula, $R_1$ and $R_9$ are independently selected from the group consisting of H, alkyl, aryl, perfluoroaryl, perfluoroalkyl, alkylaryl, alkoxyaryl, alkylcarboxyl, aryl carbonyl, haloalkyl, perfluoroalkyl, glycols, haloaryl, a negative electrolyte, and a polymer, so long as when $R_1$ is H, $R_9$ is not H. In some embodiments, $R_3$ and $R_7$ are independently selected from the group consisting of H, alkyl, perfluoroalkyl, alkylaryl, alkoxyaryl, alkylcarboxyl, aryl carbonyl, haloalkyl, perfluoroalkyl, glycols, haloaryl, a negative electrolyte, and a polymer. The term negative electrolyte is well understood to those of ordinary skill in the art. In some embodiments, $R_{10}$ is selected from the group consisting of methyl, alkyl, aryl, alkylaryl, alkoxyaryl, alkylcarboxyl, aryl carbonyl, haloalkyl, perfluoroalkyl, perfluoroaryl, glycols, haloaryl, an oligomer, and a polymer.

As will be recognized by those of ordinary skill in the art, examples of negative electrolytes include, but are not limited to, quinones, pyridines, pyrenes, nictotinamides, quinoxaline compounds, dipyridyl ketone compounds, and viologen compounds, among other electrochemically reducible conjugated organic molecules. The term polymer is also well understood to those of ordinary skill in the art. As will be recognized by those of ordinary skill in the art, examples of polymers that can be used in accordance with the presently-disclosed subject matter include, but are not limited to, oligoglycols and polyethylene glycols, polyacrylates, polycarbonates, and other polymers that are soluble in an organic solvent.

In some embodiments, the compound has the structure of formula II.

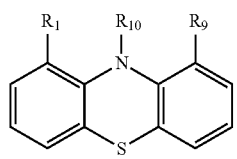

(II)

In some embodiments, the compound has the structure of formula III.

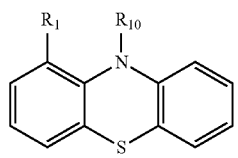

(III)

In some embodiments, the compound has the structure of formula IV.

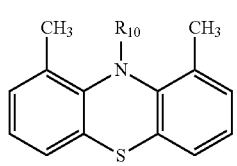

(IV)

In some embodiments, the compound has the structure of formula V.

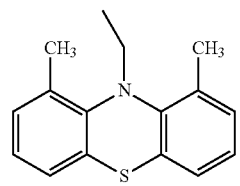

(V)

In some embodiments, the compound has the structure of formula VI.

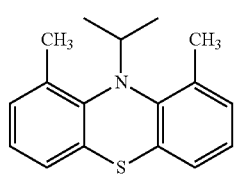

(VI)

In some embodiments, the compound has the structure of formula VII.

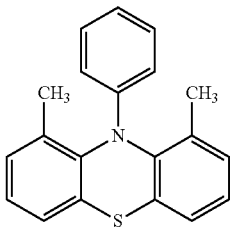

(VII)

In some embodiments, the compound has the structure of formula VIII.

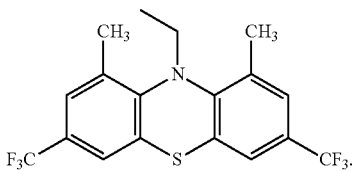

(VIII)

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
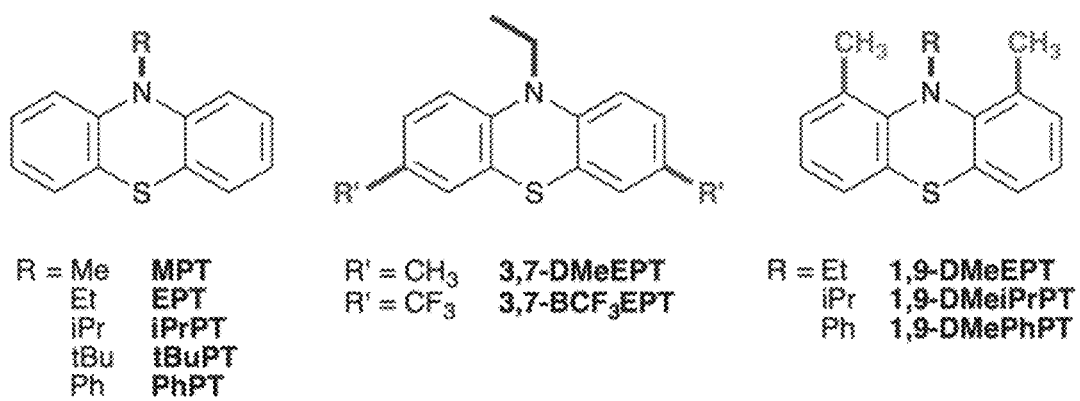
FIG. 1 depicts the structures of various phenothiazine derivatives.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes rechargeable batteries and compounds for use in such batteries. Compounds disclosed herein are useful for conferring overcharge protection, for example. Compounds disclosed herein also include those which are substantially more planar in their radical-cation states as compared to their neutral states, and which have increased oxidation potentials without requiring use of electron-withdrawing groups, leading to less-easily accessed reduction potentials.

The possibility of raising phenothiazine oxidation potentials without incorporating electron-withdrawing groups was explored by the present inventors in connection with their work on overcharge protection of lithium-ion batteries (LIBs). As detailed herein, the present inventors have demonstrated molecular design principles to dictate the relaxation processes of π-conjugated molecules through strain solely in their ionized state, while imparting minimal change to the ground-state characteristics, as an effective way to synthetically control redox potentials.

Some embodiments of the presently-disclosed subject matter include a compound which has the structure of formula I.

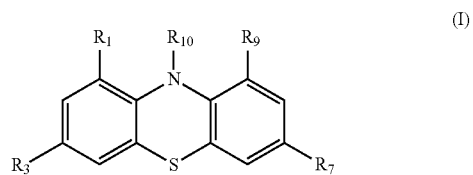

wherein

R$_1$ and R$_9$ are independently selected from the group consisting of H, alkyl, aryl, perfluoroaryl, perfluoroalkyl, alkylaryl, alkoxyaryl, alkylcarboxyl, aryl carbonyl, haloalkyl, perfluoroalkyl, glycols, haloaryl, a negative electrolyte, and a polymer, so long as when R$_1$ is H, R$_9$ is not H;

R$_3$ and R$_7$ are independently selected from the group consisting of H, alkyl, perfluoroalkyl, alkylaryl, alkoxyaryl, alkylcarboxyl, aryl carbonyl, haloalkyl, perfluoroalkyl, glycols, haloaryl, a negative electrolyte, and a polymer; and R$_{10}$ is selected from the group consisting of methyl, alkyl, aryl, alkylaryl, alkoxyaryl, alkylcarboxyl, aryl carbonyl, haloalkyl, perfluoroalkyl, perfluoroaryl, glycols, haloaryl, an oligomer, and a polymer.

In some embodiments of the compound, R$_1$ and R$_9$ are each CH$_3$ or CF$_3$. In some embodiments of the compound, R$_1$ and R$_9$ are each CH$_3$. In some embodiments of the compound, R$_1$ and R$_9$ are aryl and perfluoroaryl. In some embodiments of the compound, R$_{10}$ is H, alkyl, or aryl. In some embodiments of the compound, R$_{10}$ is methyl, ethyl, isopropyl, phenyl, aryl, or perfluoroaryl.

In some embodiments, the compound has the structure of formula II.

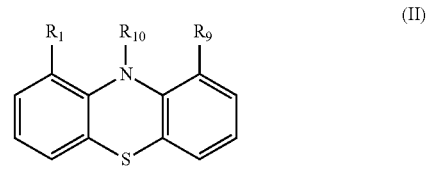

In some embodiments, the compound has the structure of formula III.

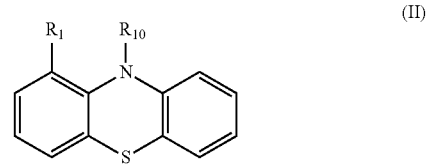

In some embodiments, the compound has the structure of formula IV.

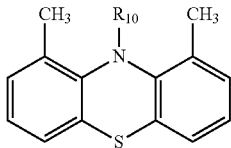

(IV)

In some embodiments, the compound has the structure of formula V.

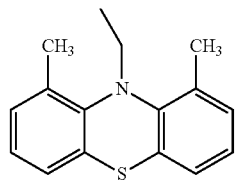

(V)

In some embodiments, the compound has the structure of formula VI.

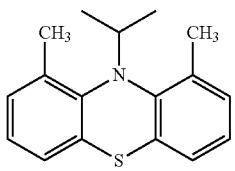

(VI)

In some embodiments, the compound has the structure of formula VII.

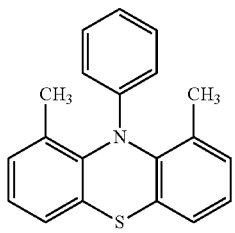

(VII)

In some embodiments, the compound has the structure of formula VIII.

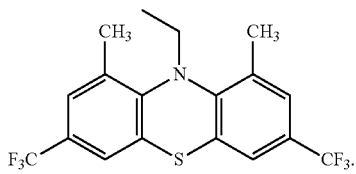

(VIII)

In defining various terms such as "R", such terms are used herein as generic symbols to represent various specific substituents. These symbols can be any sub stituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term. The term "alkyl" is inclusive of "cycloalkyl."

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

In this regard, the term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The terms "alkoxy" and "alkoxyl" as used herein to refer to an alkyl or cycloalkyl group bonded through an ether linkage; that is, an "alkoxy" group can be defined as $—OA^1$ where A' is alkyl or cycloalkyl as defined above. "Alkoxy" also includes polymers of alkoxy groups as just described; that is, an alkoxy can be a polyether such as $—OA^1—OA^2$ or $—OA^1—(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. The term is include of linear and ring-forming (i.e., cycloakenyl) groups. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, haide, hydroxy, ketone, azide, nitro, silyl, sulfo-oxo, or thiol, as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula $—C(O)H$. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein. In specific embodiments amine refers to any of $NH_2$, NH(alkyl), NH(aryl), $N(alkyl)_2$, and $N(aryl)_2$.

The term "carboxylic acid" as used herein is represented by a formula $—C(O)OH$.

The term "ester" as used herein is represented by a formula $—OC(O)A^1$ or $C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula $-(A^1O(O)C-A^2-C(O)O)_a—$ or $-(A^1O(O)C-A^2-OC(O))_a—$, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "halide," "halogen," or the like refer to the halogens fluorine, chlorine, bromine, and iodine.

The term "thiol" as used herein is represented by a formula —SH.

The term "polymer," when used herein to refer to R of the compounds disclosed herein, includes vinyl polymers, including but not limited to ethylene, propylene, and styryl polymers, cyclic alkenes, including for example norbornene, norbornadiene, cyclopentene, and cyclooctatetraene, acrylates, amines, epoxies, isocyanates, and the like. Also, as used herein, polymer refers to linear polymers as well as other arrangements, including for example, dendrimer, star, and hyper branched polymers. In some embodiments, the polymer can include phenothiazine as the sole monomer in a repeating polymer. In some embodiments, the polymer can include phenothiazine as part of a polymer that contains more than one repeat unit, e.g., alternating copolymer or block copolymer. Oligomer, as used herein to refer to R of the compounds disclosed herein, is made up of a discrete number of repeat units typically less than about 20, and in some embodiments, is about five or less repeat units or monomers.

In some embodiments, the compound can be used as a redox shuttle.

In some embodiments, the compound can be used as passivating electrolyte additives for lithium-ion, sodium-ion, and other batteries.

In some embodiments, the compound can be used as a photopolymerization initiator or photoredox catalyst.

In some embodiments, the compound can be used as an electrode material in a battery including non-aqueous redox flow batteries.

As used here, the term "redox shuttle" refers to an electrochemically reversible compound that can become oxidized at a positive electrode of a battery, migrate to a negative electrode of the battery, become reduced at the negative electrode to reform the unoxidized/less-oxidized shuttle species, and migrate back to the positive electrode. A redox shuttle can be an electroactive compound, which can be heterocyclic. A redox shuttle can protect against overcharging.

The presently-disclosed subject matter includes a rechargeable battery. In some embodiments, the rechargeable battery includes a negative electrode, a positive electrode, and an electrolyte that includes a compound as disclosed herein. In some embodiments, the positive electrode is immersed in the electrolyte. In some embodiments, the electrolyte further comprises a charge-carrying medium. In some embodiments, the electrolyte further includes a lithium salt.

In some embodiments, the rechargeable battery is a rechargeable lithium-ion battery, which includes a high-voltage cathode, a negative electrode, an electrolyte comprising a charge-carrying medium and a lithium salt, and a redox shuttle comprising a compound as disclosed herein.

The term "electrolyte" is well understood to those of ordinary skill in the art and provides a charge-carrying pathway between the negative electrode and the positive electrode. The electrolyte can include a charge-carrying medium and a lithium salt. The electrolyte can also include a redox shuttle.

In some embodiments, the battery makes use of a compound/redox shuttle at a concentration of about 0.05-0.1 M. In some embodiments, the battery makes use of a compound/redox shuttle having a solubility of about 0.5 M or greater.

The term "negative electrode" is well understood to those of ordinary skill in the art and refers to one of a pair of electrodes that, under normal circumstances and when the battery/cell is fully charged, has the lowest potential. The negative electrode that can be used in connection with the presently-disclosed subject matter is not particularly limited and can be generally selected from those known in the art, for example, a graphitic anode.

The term "positive electrode" is well understood to those of ordinary skill in the art and refers to one of a pair of electrodes that, under typical circumstances, and when the battery/cell is fully charged, will have the highest potential that it can achieve under normal operation.

As passivating electrolyte additive is a composition added that can stabilize the surface of anode, typically by forming a passivation film.

A photopolymerization initiator is a chemical species that upon exposure to light (for example, ultraviolet or visible spectrum) produces a reactive species that can react with a composition, and changes the composition in one or more properties. An exemplary photopolymerization initiator can, for example, upon exposure to light, react with a polymerizable composition to generate a cross-linked polymer.

A photoredox catalyst uses light to facilitate a chemical reaction by mediating a transfer of electrons between chemical compounds. The photoinduction of electron transfer of the catalysts allows for the activation of substrates that do not readily absorb the energy of light by themselves.

As noted herein, the presently-disclosed subject matter includes rechargeable batteries in which the positive electrode is a high-voltage cathode. Examples of high-voltage cathodes include, but are not limited to $LiFePO_4$ (LFP), $LiMn_2O_4$ (LMO), $LiCoO_2$ (LCO), $LiNi_{1/3}Mn_{1/3}Co_{1/3}O_2$ (NMC), and $LiNi_{0.8}Co_{0.15}Al_{0.05}O_2$ (NCA). A high-voltage cathode is one that can be said to have an end-of-charge potential of about 4.0 V or greater. Such high-voltage cathodes benefit from redox shuttles that oxidize at potentials of at least about 4.0, 4.1, 4.2, 4.3, 4.4, 4.5, 4.6, or 4.7 to about 4.8 V as compared to $Li/Li^+$.

In some embodiments of the presently-disclosed subject matter, the battery makes use of a compound that oxidizes at a potential of about 3.7 V to about 5.0 V as compared to $Li/Li^+$. In some embodiments of the presently-disclosed subject matter, the battery makes use of a compound that oxidizes at a potential of about 4.0 V to about 4.8 V as compared to $Li/Li^+$. In some embodiments, the compound oxidizes at a potential of about 4.2 V to about 4.5 V. In some embodiments, the compound oxidizes at a potential of about 4.2 V to about 4.3 V.

The presently-disclosed subject matter is further inclusive of an article that includes a battery as disclosed herein.

Batteries connected in series can be particularly vulnerable to overcharge. The presently-disclosed subject matter is inclusive of an array that includes two or more batteries as disclosed herein. In some embodiments, the array includes two or more batteries connected in a series.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC Nomenclature.

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples as set forth by the present inventors. The following examples may include compilations of data that are representative of data gathered at various times during the course of development and experimentation related to the present invention.

EXAMPLES

Example 1

Inspired by studies of molecular strain, the strategic placement of substituents on the phenothiazine core was investigated for use to tune molecular redox characteristics through geometric constraints, with minimal impact of the substituent electronic effects. Deliberate incorporation of substituents around the periphery of the phenothiazine core was also tested for ability to disrupt the relaxation of the radical-cation state, thereby increasing the oxidation potential when compared to the unsubstituted system.

Derivatives of N-substituted phenothiazines where substituents were incorporated at positions ortho to the nitrogen atom (1 and 9 positions) were evaluated for capability to prevent planarization of the oxidized species through steric interactions with the N-alkyl group.

The electrochemical characteristics of these derivatives were compared to a parent compound with only an N substituent, and to derivatives where the same substituents are incorporated at positions para to the nitrogen atom (3 and 7 positions) so that planarization in the oxidized state remains possible and the full electronic effects of the substituents would be in play. For the sake of clarity, these Examples will focus discussion on the N-ethyl derivatives, where EPT is the parent, 1,9-DMeEPT the crowded derivative, and 3,7-DMeEPT the uncrowded analogue (FIG. 1).

At the outset of the investigation, density functional theory (DFT) calculations were performed at the B3LYP/6-311G(d,p) level to predict molecular geometries in the neutral and radical-cation states and the adiabatic and vertical ionization potentials (IPs) of various substituted phenothiazines.

The neutral geometries of EPT, 3,7-DMeEPT, and 1,9-DMeEPT are quite similar, with the butterfly angles showing little variation (139-143°). However, as radical cations, EPT and 3,7-DMeEPT are significantly more planar(171°) than 1,9-DMeEPT(157° (Table 1); note that 180° represents a fully planar phenothiazine. Similar trends are noted for the other 3,7- and 1,9-substituted phenothiazines in the series.

TABLE 1

Adiabatic ionization potentials (IP), half-wave first oxidation potentials ($E_{1/2}^{+/0}$) vs. $Cp_2Fe^{+/0}$, and neutral and radical cation butterfly angles.

| Compound | IP (eV)[a] | $E_{1/2}^{+/0}$ (V)[b] | Butterfly Angles (°)[a] | |
|---|---|---|---|---|
| | | | Neutral | Radical Cation |
| MPT | 6.58 | 0.31[e] | 143.4 (143.7)[d] | 165.2 (177.8) |
| EPT | 6.48 | 0.27 | 138.7 (136.8)[d] | 171.4 (173.8) |
| iPrPT | 6.52 | 0.33[e] | 142.6 (137.9)[e] | 160.7 |
| tBuPT | 6.67 | 0.53[e] | 134.2 (135.0)[e] | 148.3 |
| PhPT | 6.34 | 0.26[e] | 149.5 (162.3)[e] | 180.0 |
| 3,7-DMeEPT | 6.24 | 0.13[f] | 138.8 (149.3)[f] | 171.1 |
| 3,7-BCF3EPT | 7.06 | 0.61[f] | 139.7 (144.5-152.1)[g] | 171.1 (164.5)[g] |
| 1,9-DMeEPT | 6.68 | 0.55 | 143.1 (146.5) | 156.6 |
| 1,9-BCF3EPT | 7.21 | — | 141.8 | 159.0 |
| 1,9-DMeiPrPT | 6.76 | 0.68 | 132.5 (134.1) | 147.5 |
| 1,9-DMePhPT | 6.85 | 0.86[c] | 132.4 (134.9) | 137.2 |

[a]DFT calculations at the B3LYP/6-311(d,p) level of theory; X-ray crystallographic values in parentheses.
[b]CV performed with 1.6 mM in 0.1M nBu4NPF6/DCM at 100 mV/s.
[c]Oxidation was irreversible.
[d]Reference[11].
[e]Reference[7b].
[f]Reference[9d].
[g]Multiple molecules present in asymmetric unit, reference[12].

A series of phenothiazine derivatives have been studied, where the geometry of the oxidized (radical-cation) state tends to be planar, while the neutral ground state is bent.[7] In particular, for N-substituted phenothiazines (FIG. 1, left), the present inventors observed a correlation in the degree of molecular bending (referred to as the "butterfly angle") of the radical-cation geometry and the ease of oxidation: From ethyl to iso-propyl to tert-butyl (EtPT, iPrPT, tBuPT), the increased substituent size led to a larger radical-cation butterfly angle and higher-potential oxidation events (Table 1). Importantly, this effect is opposite to what one would predict based on the Hammett constants of the substituents, suggesting that preventing planarization in radical cations may raise oxidation potentials, regardless of the substituent's Hammett constant.

DFT calculations predict 3,7-DMeEPT to have an adiabatic IP 0.24 eV smaller than EPT, consistent with measured oxidation potentials[9c] and expectations based on the electron-donating capability of a methyl group. However, 1,9-DMeEPT has an IP 0.20 eV larger than EPT (Table 1). Thus, for the two DMeEPT constitutional isomers, we observe a difference in IP of 0.44 eV. The IP trends are similar for 3,7-BCF3EPT and 1,9-BCF3EPT, with 1,9-BCF3EPT having a larger IP, though the IP range is smaller (0.15 V). These results showcase the considerable impact that steric crowding of the radical-cation state can have in order to increase the IP.

Figure 2:
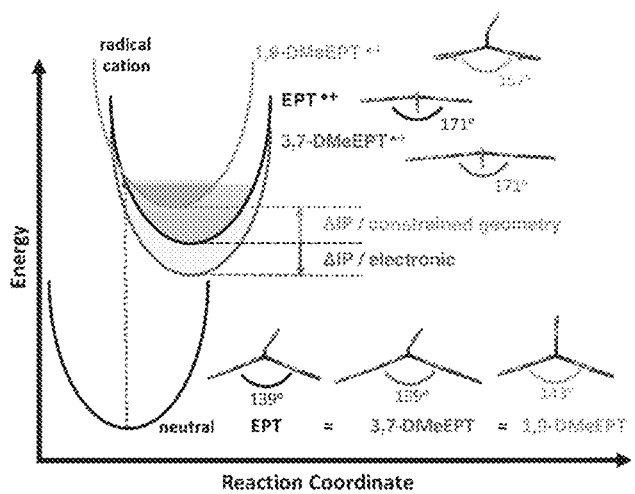
FIG. 2 includes representations of the potential energy surfaces for the oxidation of EPT, 3,7-DMeEPT, and 1,9-DMeEPT. The gray arrow with a dotted line depicts the vertical ionization process from ground-state, neutral species. Shaded regions represent relaxation energies in the radical-cation potential energy surfaces. The change in IP is given by ΔIP.

Similar trends are observed for the vertical IPs (Table 2). Notably, the relaxation energy (λ) in the radical-cation potential energy surface is smaller for 1,9-DMeEPT (at 0.27 eV) than for EPT and 3,7-DMeEPT (both at 0.40 eV), signifying the impact of the methyl groups at the 1 and 9 positions in limiting radical cation relaxation to a more planar configuration. Moreover, the vertical IPs for EPT and 1,9-DMeEPT are quite similar (differing by 0.07 eV), while that of 3,7-DMeEPT is much smaller than EPT (by 0.23 eV), revealing the differences in the electronic impact of methyl substituents in the 1 and 9 vs. 3 and 7 positions. Potential energy surfaces displaying these differences in terms of the adiabatic and vertical IPs and relaxation energies are represented in FIG. 2.

TABLE 2

Select frontier molecular orbital energies, vertical and adiabatic ionization potentials (VIP and AIP, respectively), and relaxation energies in the radical-cation potential energy surface ($\lambda_{IP}$) for select phenothiazine derivatives as determined at the B3LYP/6-311G(d, p) level of theory.

| Compound | HOMO-1 (eV) | HOMO (eV) | LUMO (eV) | AIP (eV) | VIP (eV) | $\lambda_{IP}$ (eV) |
|---|---|---|---|---|---|---|
| MPT | −6.30 | −5.27 | −0.61 | 6.58 | 6.87 | 0.29 |
| EPT | −6.26 | −5.30 | −0.56 | 6.48 | 6.88 | 0.40 |
| iPrPT | −6.23 | −5.22 | −0.57 | 6.52 | 6.77 | 0.25 |
| tBuPT | −6.20 | −5.39 | −0.55 | 6.67 | 6.93 | 0.25 |
| PhPT | −6.24 | −5.16 | −0.91 | 6.34 | 6.68 | 0.33 |
| 3,7-DMeEPT | −6.12 | −5.15 | −0.46 | 6.24 | 6.65 | 0.40 |
| 3,7-BCF3EPT | −6.94 | −5.96 | −1.44 | 7.06 | 7.49 | 0.43 |
| 1,9-DMeEPT | −6.14 | −5.40 | −0.51 | 6.68 | 6.95 | 0.27 |
| 1,9-BCF3EPT | −6.83 | −5.96 | −1.40 | 7.21 | 7.52 | 0.31 |
| 1,9-DMeiPrPT | −6.35 | −5.69 | −0.56 | 6.76 | 7.25 | 0.49 |
| 1,9-DMePhPT | −6.08 | −5.55 | −0.76 | 6.85 | 7.00 | 0.15 |

TABLE 3

$S_0 \to S_1$ vertical transition energies, oscillator strengths (f), and electronic configurations for select phenothiazine derivatives as determined with TDDFT at the B3LYP/6-311G(d,p) level of theory.

| | Neutral | | |
|---|---|---|---|
| Compound | $S_0 \to S_1$ (nm, eV) | f | Configuration |
| EPT | 322 (3.85) | 0.0003 | HOMO → LUMO (98%) |
| 3,7-DMeEPT | 322 (3.85) | 0.0004 | HOMO → LUMO (5%) HOMO → LUMO + 1 (92%) |
| 1,9-DMeEPT | 310 (4.00) | 0.0052 | HOMO → LUMO (97%) |
| 1,9-DMeiPrPT | 287 (4.33) | 0.0148 | HOMO → LUMO (91%) |
| 1,9-DMePhPT | 309 (4.02) | 0.0327 | HOMO → LUMO (98%) |

TABLE 4

$D_1 \to D_2$ vertical transition energies, oscillator strengths (f), and electronic configurations for select phenothiazine derivatives as determined with TDDFT at the B3LYP/6-311G(d,p) level of theory.

| | Radical Cation | | |
|---|---|---|---|
| Compound | $D_1 \to D_2$ (nm, eV) | f | Configuration |
| EPT | 773 (1.60) | 0.0146 | HOMO-1 → SOMO (98%) |
| 3,7-DMeEPT | 755 (1.64) | 0.0112 | HOMO-1 → SOMO (98%) |
| 1,9-DMeEPT | 1024 (1.21) | 0.0105 | HOMO-1 → SOMO (99%) |
| 1,9-DMeiPrPT | 1127 (1.10) | 0.0098 | HOMO-1 → SOMO (99%) |
| 1,9-DMePhPT | 1564 (0.79) | 0.0275 | HOMO-1 → SOMO (99%) |

Figure 3:
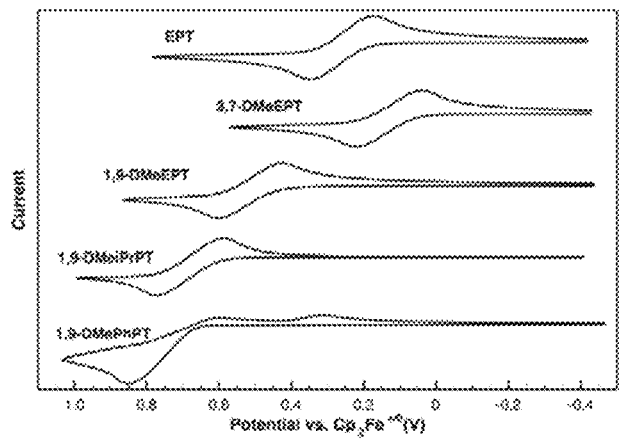
FIG. 3 shows cyclic voltammograms of EPT, 3,7-DMeEPT, 1,9-DMeEPT, 1,9-DMeiPrPT, and 1,9-DMePhPT at 1.6 mM in 0.1 M nBu$_4$NPF$_6$ in DCM. Voltammograms are calibrated to Cp$_2$Fe$^{+/0}$ at 0 V, and recorded at 100 mV/s.

With computational results in hand that supported our hypothesis, 1,9-DMeEPT and related N-iso-propyl (1,9-DMeiPrPT) and N-phenyl (1,9-DMePhPT) derivatives (FIG. 1) were prepared for further study. Solid-state butterfly angles show good agreement with DFT calculations (Table 1). Importantly, the trends in oxidation potentials from CV experiments (FIG. 3) validated our hypothesis and computational results. Unlike 3,7-DMeEPT, which is more easily oxidized than EPT (by 0.13 V), 1,9-DMeEPT is harder to oxidize than EPT (by 0.28 V). Moreover, as the size of the radical-cation butterfly angle within the series of 1,9-dimethyl-substituted phenothiazines, the oxidation potentials increase further. Of the three 1,9-dimethyl-substituted derivatives, 1,9-DMePhPT has the highest oxidation potential. Notably, this trend does not follow that of the solely N-substituted equivalents (iPrPT is harder to oxidize than both EPT and PhPT),[7b] though within each series of three compounds, the oxidation potentials follow the same trends as the calculated adiabatic IPs and radical-cation butterfly angles. Furthermore, scans of the full electrochemical window (FIG. 4) show that reduction events remain inaccessible throughout the series, with solvent reduction occurring before a reduction event could be observed.

Figures 5A, 5B:
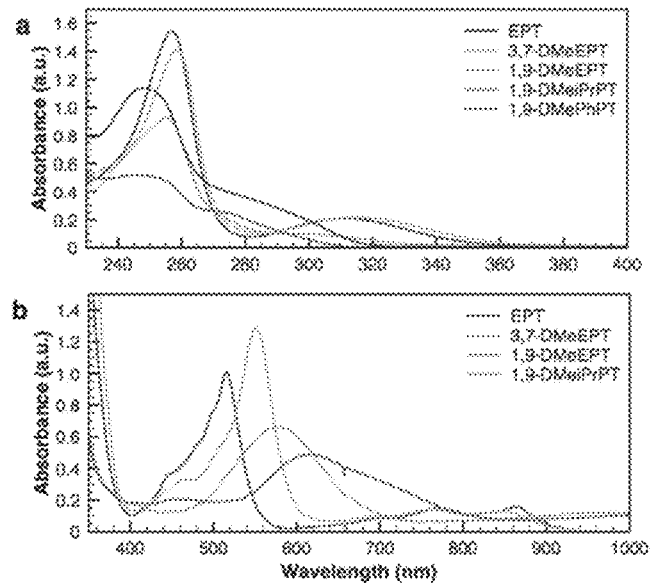
FIGS. 5a and 5b are UV-vis absorption spectra of EPT, 3,7-DMeEPT, 1,9-DMeEPT, 1,9-DMeiPrPT, and 1,9-DMePhPT in their neutral (a) and radical cation (b) forms at 14 μM and 0.1 mM, respectively, in DCM. Note: No spectrum is reported for the 1,9-DMePhPT radical cation due to its irreversible first oxidation event.

UV-vis absorption spectroscopy was used to explore electronic transitions in the neutral and radical-cation states. While the absorption profiles of neutral EPT and 3,7-DMeEPT are nearly identical, the absorption onsets of the 1,9-dimethyl-substituted derivatives are slightly blue-shifted (FIG. 5a). These changes in energy, although small, are consistent with trends in the energy of the $S_0 \to S_1$ transition energy determined by time-dependent DFT (TD-DFT) calculations (Table 2). UV-vis spectra of the radical cations, generated by chemical oxidation, further reflect differences in the oxidized species (FIG. 5b). The absorption spectra of the radical cations of EPT and 3,7-DMeEPT show profiles consistent with the radical cations of several phenothiazine derivatives prepared in our laboratory: intense absorption features between 500-600 nm and low-energy, low-intensity bands between 650-950 nm.[7b,13] By contrast, the analogous absorption features for the 1,9-disubstituted derivatives occur at lower energies. These trends in transition energies are confirmed by TD-DFT calculations (Table 2). Our results suggest that variation in placement of methyl groups affects the electronic gap between the HOMO-1 and HOMO (using the nomenclature of the neutral species), which in turn influences the $D_1 \to D_2$ transition of the radical cation that is predominately HOMO-1→SOMO (singly-occupied molecular orbital) in nature. From DFT calculations, the HOMO of EPT and 1,9-DMeEPT are nearly isoenergetic, while that of 3,7-DMeEPT is energetically destabilized; this is consistent with the trends of the computed vertical IPs, confirming the validity of a Koopmans' theorem[14] (Janak's theorem[15] in the context of DFT) estimate of the verticals IP based on the HOMO energies. However, the HOMO-1 of 3,7-DMeEPT and 1,9-DMeEPT are of similar energy and energetically destabilized when compared to EPT, revealing the comparable electronic impact of the methyl groups on the HOMO-1 regardless of the methyl group location on the phenothiazine. The combination of these effects results in a smaller HOMO-1 to HOMO energy gap for 1,9-DMeEPT, which is found here to translate to a smaller first-excited-state transition energy of the radical cation.

In summary, by positioning traditionally electron-donating substituents in close proximity to the N substituent, the relaxation of the phenothiazine radical-cation state was disrupted with increased the oxidation potentials relative to their counterparts that are able to fully relax. This approach offers a strain-induced modulation of electrochemical properties orthogonal to conventional tuning by substituent character. The aim is to identify new organic materials with higher oxidation potentials while limiting access to reduction events by disrupting relaxation pathways in fused-ring systems.

Example 2

2-Bromotoluene was purchased from Oakwood Products. Urea, bromoethane, 2-bromopropane, tetrabutylammonium hexafluorophosphate, tris(4-bromophenyl)aminium hexachloroantimonate, anhydrous toluene, and anhydrous p-dioxane were purchased from Sigma Aldrich. Phenothiazine, sodium hydride (60% dispersion in mineral oil), bis(dibenzylideneacetone)palladium(0), sodium tert-butoxide, sulfur, iodine, o-dichlorobenzene (ODCB), anhydrous dichloromethane (DCM), anhydrous tetrahydrofuran, anhydrous N,N-dimethylformamide (DMF), and magnesium sulfate were obtained from Acros Organics. Tri-tert-butylphosphonium tetrafluoroborate was obtained from Oxchem. Silica gel and neutral alumina used for column chromatography were purchased from Silicycle and Sorbent Technologies, respectively. Ethyl acetate, hexanes, and diethyl ether were purchased from VWR. Solvents used for NMR spectroscopy were obtained from Cambridge Isotope Laboratories.

Example 3

N-Ethylphenothiazine[16] and N-ethyl-3,7-dimethylphenothiazine[17] were prepared as previously reported.

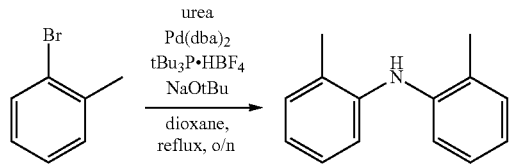

Bis(o-tolyl)amine

This compound was synthesized by modifying a previously reported procedure.[18] To an oven-dried 350 mL pressure vessel were added 2-bromotoluene (3.62 mL, 30.1 mmol), urea (0.90 g, 14.9 mmol), sodium tert-butoxide (6.62 g, 68.9 mmol), and anhydrous dioxane (70 mL). The reaction mixture was sparged with $N_2$ for 15 min. Bis(dibenzylideneacetone)palladium(0) (0.092 g, 0.15 mmol) and tri-tert-butylphosphonium tetrafluoroborate (0.087 g, 0.30 mmol) were added and after sparging with Na for an additional 10 min, the reaction vessel was sealed with a PTFE screw cap. The pressure vessel was immersed in an oil bath heated to 100° C. and was stirred overnight. The reaction mixture was then removed from the oil bath and allowed to cool to room temperature. Water was added to the reaction mixture, and the product was extracted with ethyl acetate, washed with brine, and dried over magnesium sulfate ($MgSO_4$). The organic layer was filtered to remove solids and was concentrated by rotary evaporation. The crude product was passed through a short pad of alumina, eluting with hexanes to afford the product as a pale yellow oil (2.50 g, 84%). $^1$H NMR (400 MHz, $CDCl_3$) δ 7.17 (d, J=7.4 Hz, 2H), 7.09 (t, J=7.6 Hz, 2H), 6.97 (d, J=8.0 Hz, 2H), 6.88 (t, J=7.4 Hz, 2H), 5.11 (s, 1H), 2.24 (s, 6H). $^{13}$C NMR (100 MHz, $CDCl_3$) 5142.0, 130.9, 127.6, 126.9, 121.5, 118.4, 17.9.

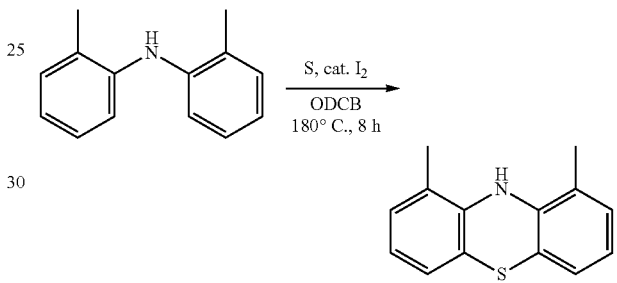

1,9-Dimethylphenothiazine (1,9-DMePT)

This compound was synthesized following a slightly modified version of a reported procedure.[19] To an oven-dried pressure tube cooled under Na, bis(o-tolyl)amine (2.70 g, 13.7 mmol), sulfur (1.09 g, 34.2 mmol), iodine (0.0510 g, 0.402 mmol), and ODCB (2 mL) were added. The pressure tube was sealed with a Teflon cap, and the reaction mixture was immersed in an oil bath heated to 180° C. for 8 h. After removing the reaction flask from the oil bath, the reaction mixture was allowed to cool to room temperature. It was then diluted with ethyl acetate and water, and the precipitate was removed via filtration. The organic layer was separated from the aqueous layer and washed with brine. The organic layer was then dried over $MgSO_4$, filtered, and concentrated by rotary evaporation. The resulting crude material was purified by column chromatography over neutral alumina using a gradient of hexanes and ethyl acetate to elute the product, which was crystallized from ethanol (0.81 g, 26%). $^1$H NMR (400 MHz, $CD_3CN$) δ 6.94 (d, J=7.7 Hz, 2H), 6.85 (d, J=7.7 Hz, 2H), 6.76 (t, J=7.5 Hz, 2H), 6.02 (br, 1H), 2.25 (s, 6H). $^{13}$C NMR (100 MHz, CD3CN) 5141.2, 130.1, 125.4, 123.8, 123.3, 118.9, 17.1. Anal. calcd. for $C_{14}H_{13}NS$ C, 73.97; H, 5.76; N, 6.16. Found C, 73.67; H, 5.79; N, 6.06.

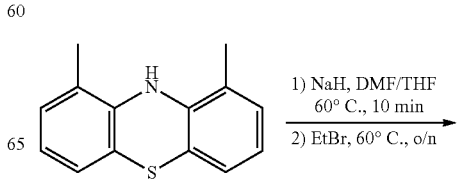

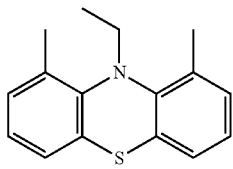

Synthesis of N-ethyl-1,9-dimethylphenothiazine (1,9-DMeEPT)

In an oven-dried 50 mL round-bottomed flask equipped with a reflux condenser under a Na atmosphere, 1,9-dimethylphenothiazine (0.542 g, 2.39 mmol) was dissolved in a solution of anhydrous DMF (8 mL) and anhydrous THF (8 mL). Sodium hydride (0.202 g, 60 wt. % in mineral oil, 5.05 mmol) was added at room temperature, and the reaction was stirred for 10 min. Bromoethane (0.90 mL, 12 mmol) was added to the reaction mixture, which was then heated to reflux in an oil bath set at 90° C. for 12 h. The reaction mixture was cooled to room temperature and quenched with ice water. The reaction mixture was then extracted with ethyl acetate, and the organic layer was washed with brine and dried over MgSO$_4$. The organic extracts were filtered and concentrated by rotary evaporation. The resulting organic residue was purified by silica gel column chromatography using a gradient of 0-10% ethyl acetate in hexanes as eluent to afford 0.142 g (23%) of a white solid. The purified product was further crystallized from aqueous ethanol to afford white crystals. $^1$H NMR (400 MHz, CDCl$_3$) δ 7.07 (d, J=7.9 Hz, 4H), 6.97 (dd, J=8.0, 7.1 Hz, 2H), 3.45 (q, J=7.1 Hz, 2H), 2.41 (s, 6H), 1.07 (t, J=7.2 Hz, 3H). $^{13}$C NMR (100 MHz, CDCl$_3$) δ 144.6, 134.9, 134.6, 129.7, 125.2, 125.1, 77.8, 77.7, 77.5, 77.2, 50.0, 18.9, 14.7. GC-MS: m/z 255 (24%), 226 (100%). Anal. calcd. for C$_{16}$H$_{17}$NS C, 75.25; H, 6.71; N, 5.38. Found C, 74.95; H, 6.73; N, 5.42.

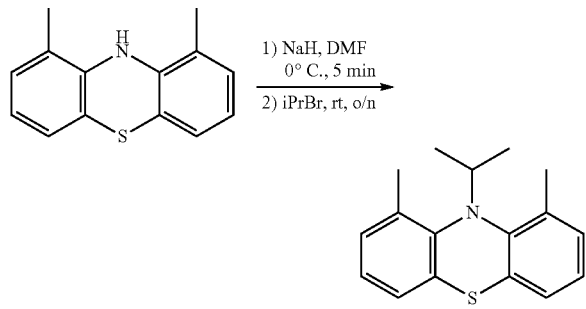

1,9-Dimethyl-N-iso-propylphenothiazine (1,9-DMeiPrPT)

To an oven-dried 25 mL round-bottomed flask cooled under Na was added 1,9-dimethylphenothiazine (0.50 g, 2.2 mmol) and anhydrous DMF (5 mL). The solution was immersed in an ice-water bath, after which sodium hydride (0.116 g, 60 wt. % in mineral oil, 4.84 mmol) was added. After stirring the suspension for 5 min, 2-bromopropane (0.81 g, 6.59 mmol) was added into the reaction mixture. The reaction was allowed to warm to room temperature and was stirred for 12 h. Ice was added to the reaction mixture, and the resulting precipitate was dissolved in diethyl ether. The organic layer was separated from the aqueous layer, washed with water and brine, dried over MgSO$_4$, and concentrated by rotary evaporation. The crude material was purified by column chromatography over silica gel using hexanes as the eluent, then crystallized from aqueous ethanol, yielding the product as a white crystalline solid (0.25 g, 42%). $^1$H NMR (400 MHz, CD$_3$CN) δ 7.22 (dd, J=7.9, 0.6 Hz, 2H), 7.17 (m, 2H), 7.05 (t, J=7.6 Hz, 2H), 3.79 (heptet, J=6.4 Hz, 1H), 2.51 (s, 6H), 1.00-0.92 (d, 6H). $^{13}$C NMR (100 MHz, CD$_3$CN) δ 145.2, 138.9, 137.2, 130.0, 126.22, 126.18, 53.5, 22.5, 19.1. GC-MS: m/z 269 (8%), 226 (100%). Anal. calcd. for C$_{18}$H$_{21}$NS C, 75.79; H, 7.11; N, 5.20. Found C, 75.52; H, 7.12; N, 5.18.

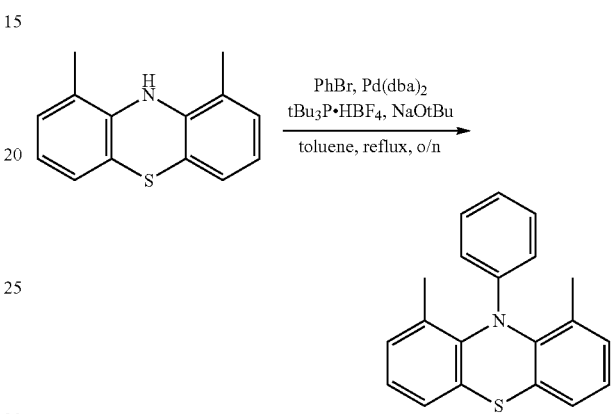

1,9-Dimethyl-N-phenylphenothiazine (1,9-DMePhPT)

To an oven-dried 15 mL pressure vessel with stir bar, 1,9-dimethylphenothiazine (0.45 g, 2.0 mmol), bromobenzene (1.57 g, 10.0 mmol), and anhydrous toluene (5 mL) were added, and the resulting solution was sparged with Na for 10 min. Sodium tert-butoxide (0.29 g, 3.0 mmol), bis(dibenzylideneacetone)palladium(0) (0.028 g, 0.050 mmol), and tri-tert-butylphosphonium tetrafluoroborate (0.030 g, 0.10 mmol) were added, and the reaction was sealed with a PTFE screw cap. The reaction flask was immersed in an oil bath heated to 120° C. for 36 h with stirring, after which the flask was removed from the oil bath and allowed to cool to room temperature. Water was added to the reaction mixture, and the product was extracted from the aqueous layer with diethyl ether. The combined organic extracts were washed with brine, dried over MgSO$_4$, filtered to remove solids, and concentrated by rotary evaporation. The crude product was purified by silica gel column chromatography using 0.5% diethyl ether in cyclohexane to afford the desired product as a white solid (153 mg, 25%). The product was crystallized using aqueous ethanol to afford a white crystalline solid. $^1$H NMR (400 MHz, CDCl$_3$) δ 7.39 (d, J=7.6 Hz, 2H), 7.28 (t, J=3.9 Hz, 3H), 7.17 (dt, J=16.0, 8.0 Hz, 4H), 6.85 (t, J=7.3 Hz, 1H), 6.42 (d, J=8.1 Hz, 2H), 2.51 (s, 6H). $^{13}$C NMR (100 MHz, CDCl$_3$) δ 144.9, 141.3, 138.0, 137.5, 129.1, 129.0, 126.7, 126.5, 119.6, 113.1, 77.5, 77.4, 77.2, 76.8, 18.4. GC-MS: m/z 226 (77%), 303 (100%). Anal. calcd. for C$_{20}$H$_{17}$NS: C, 79.17; H, 5.65; N, 4.62. Found C, 79.26; H, 5.62; N, 5.72.

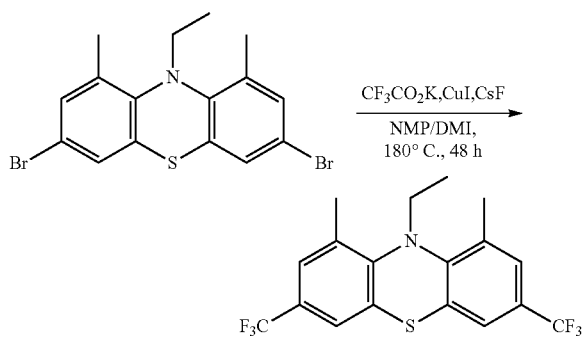

N-ethyl-1,9-dimethyl-3,7-bis(trifluoromethyl)phenothiazine (1,9-DMe-3,7 BCF3EPT)

1,9-DMe-3,7-DBrEPT (1.25 g, 3.03 mmol) and Copper(i) iodide (4.61 g, 24.2 mmol) were added in to an oven dried 100 mL pressure vessel under a Na atmosphere. The pressure vessel was transferred to an argon filled glove box, then potassium trifluoroacetate (2.76 g, 18.2 mmol) and cesium fluoride (0.99 g 6.50 mmol) were added into the pressure vessel and removed it from the glove box. N-Methylpyrrolidinone (NMP) (44 mL) and 1,3-Dimethyl-2-imidazolidinone (10 mL) were added under Na atmosphere to the reaction mixture and purged with Na for 10 min in preheated (90° C.) oil bath. Pressure vessel was sealed and increased the temperature up to 180° C. stirred for 48 h. Reaction mixture was cooled to room temperature, diluted with ethyl acetate and filtered through celite. Then water was added to the filtrate and organic product was extracted with ethyl acetate. The combined organic layers were washed with brine and dried over $MgSO_4$. The organic extracts were filtered and concentrated by rotary evaporation. The resulting organic crude was purified by silica gel column chromatography using a gradient of 0-2% ethyl acetate in hexanes as eluent, yielding the product as a white crystalline solid (0.6 g, 48%). $^1$H NMR (400 MHz, DMSO-$d_6$) δ 7.58-7.51 (m, 4H), 3.57 (q, J=7.1 Hz, 2H), 2.43 (s, 6H), 0.99 (t, J=7.1 Hz, 3H). $^{19}$F NMR (400 MHz, Chloroform-d) δ-65.39 (s, 6H). GCMS: m/z 391 (23%), 362 (100%), 330 (8%). Anal. Calcd. for $C_{18}H_{15}F_6NS$: C, 55.24; H, 3.86; F, 29.13; N, 3.58; S, 8.19. Found C, 55.04; H, 4.05; N, 3.60.

Example 4

Figure 6:
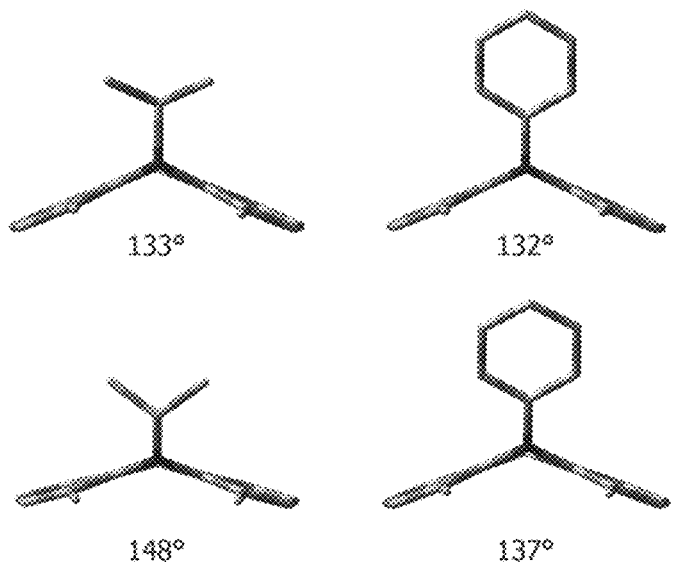
FIG. 6 depicts minimized structures and butterfly angles for the neutral (top) and radical cation (bottom) states of 1,9-DMeiPrPT and 1,9-DMePhPT obtained from DFT calculations at the B3LYP/6-311G(d,p) level of theory.
Figure 7:
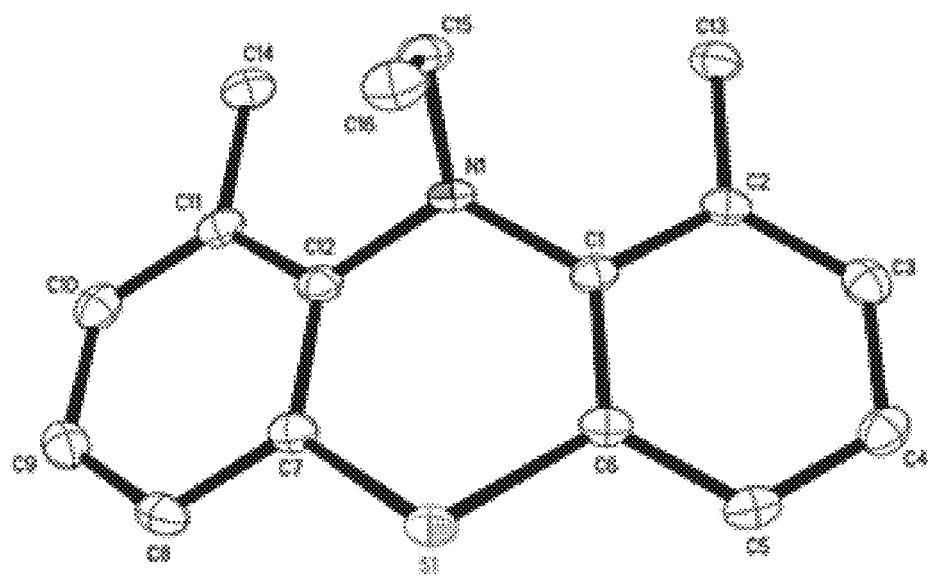
FIG. 7 includes a thermal ellipsoid plot for the 1,9-DMeEPT molecule.
Figure 8:
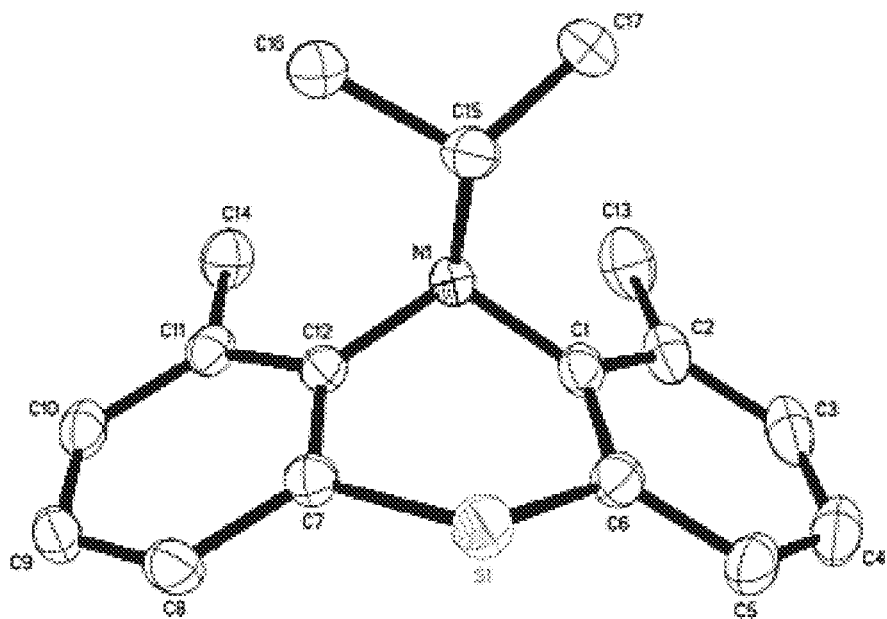
FIG. 8 includes a thermal ellipsoid plot for the 1,9-DMeiPrPT molecule.
Figure 9:
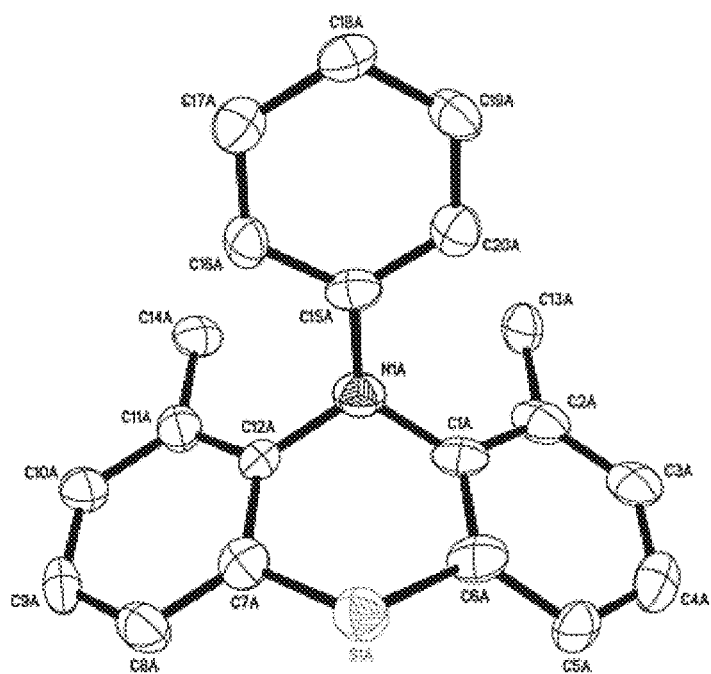
FIG. 9 includes a thermal ellipsoid plot for one molecule of 1,9-DMePhPT. This structure contained four chemically equivalent but crystallographically independent molecules.
Figure 10:
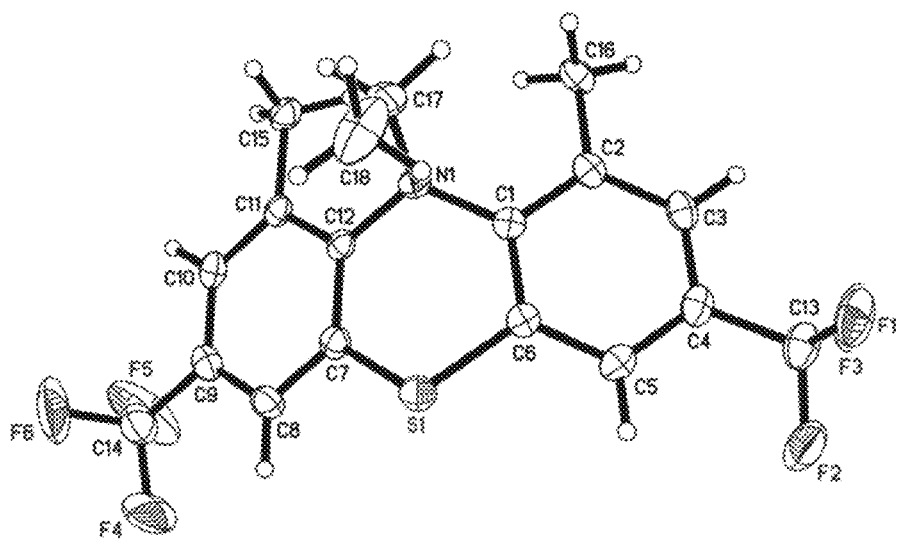
FIG. 10 includes a thermal ellipsoid plot for one molecule of N-ethyl-1,9-dimethyl-3,7-bis(trifluoromethyl)phenothiazine.

Computational Studies. All density functional theory (DFT) calculations were performed using the Gaussian09 (Revision A.02b) software suite.[20] Geometry optimizations of the neutral and radical-cation states were carried out with the B3LYP functional[21,22] and 6-311G(d,p) basis set. Frequency analyses of all (fully relaxed) optimized geometries were performed to ensure that the geometries were energetic minima. Reference is made to FIG. 6.

Example 5

X-Ray Crystallography. X-ray diffraction data were collected on either a Nonius kappaCCD diffractometer (MoKα X-rays: 1,9-DMeiPrPT) or a Bruker-Nonius X8 Proteum diffractometer (CuKα X-rays: 1,9-DMeEPT, 1,9-DMePhPT). Raw data were integrated using the Denzo-SMN package[23] (kappaCCD) or by APEX2 (X8 Proteum).[24] Scaling and merging for all datasets were performed using SADAB S.[25] All structures were solved using SHELXT[26] and refined with SHELXL-2014/7.[27] Hydrogen atoms were included using the riding-model approximation. Non-hydrogen atoms were refined with anisotropic displacement parameters. Atomic scattering factors were taken from the International Tables for Crystallography, vol. C.[28] Reference is made to FIGS. 7-10.

Example 6

Electrochemical Analysis. Cyclic voltammetry (CV) experiments were performed with a CH Instruments 600D potentiostat using a three-electrode system with glassy carbon as the working electrode, freshly anodized Ag/AgCl as the reference electrode, and a Pt wire as the counter electrode. Each solution contained 1.6 mM analyte and 0.1 M TBAPF$_6$ in DCM. Voltammograms were recorded at a scan rate of 100 mV/s. Oxidation potentials are reported relative to ferrocenium/ferrocene)($Cp_2Fe^{+/0}$. To calibrate samples, ferrocene or decamethylferrocene was used as an internal reference.

Figure 11:
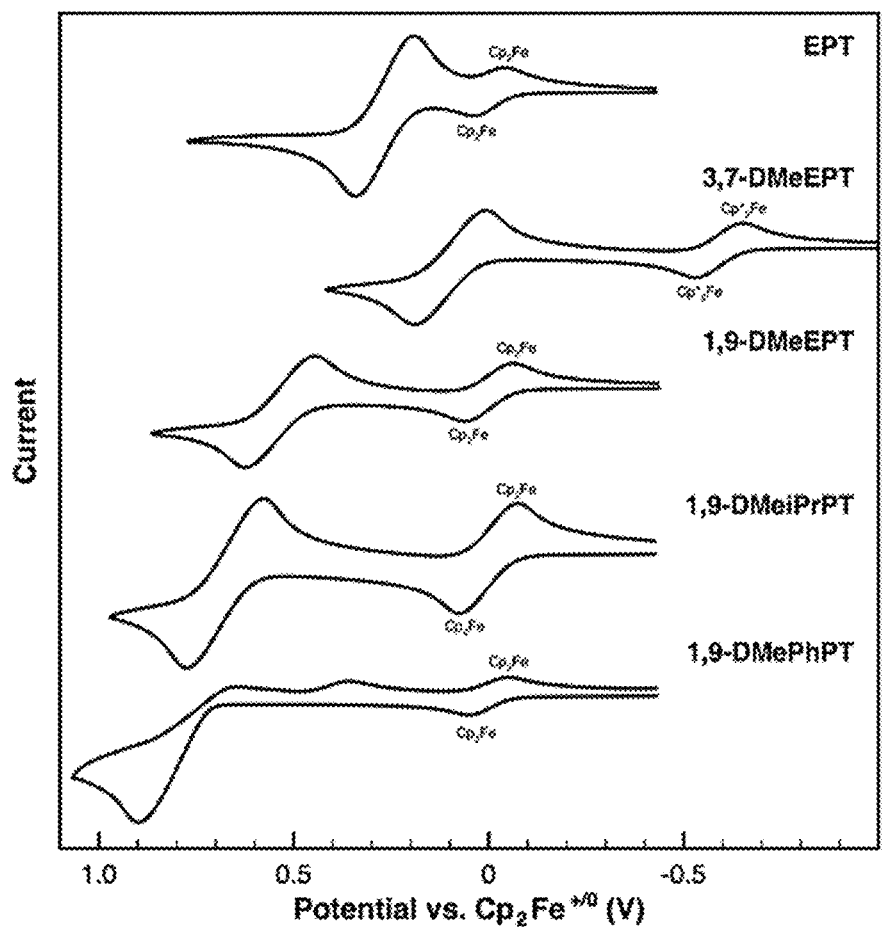
FIG. 11 includes cyclic voltammograms of EPT, 3,7-DMeEPT, 1,9-DMeEPT, 1,9-DMeiPrPT, and 1,9-DMePhPT at 1.6 mM in 0.1 M nBu$_4$NPF$_6$ in DCM vs. Cp$_2$Fe$^{+/0}$ at 0 V, containing ferrocene or decamethylferrocene as an internal reference, recorded at scan rates of 100 mV/s.
Figure 12A:
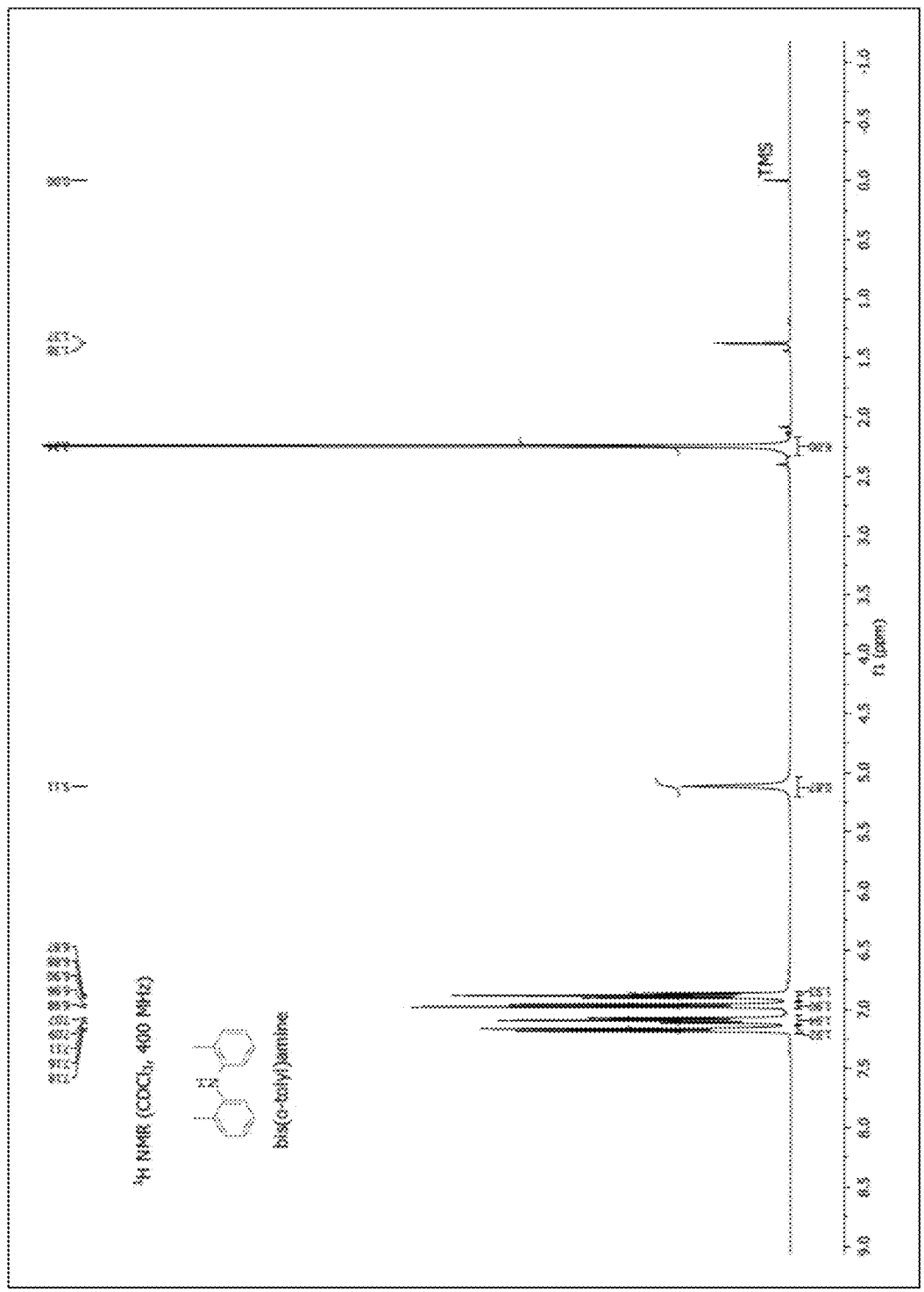
FIGS. 12a-12e are $^1$H and $^{13}$C NMR spectra of the neutral compounds of (a) Bis(o-tolyl)amine, (b) 1,9-DMePT, (c) 1,9-DMeEPT, (d) 1,9-DMeiPrPT, and (e) 1,9-DMePhPT.
Figure 12B:
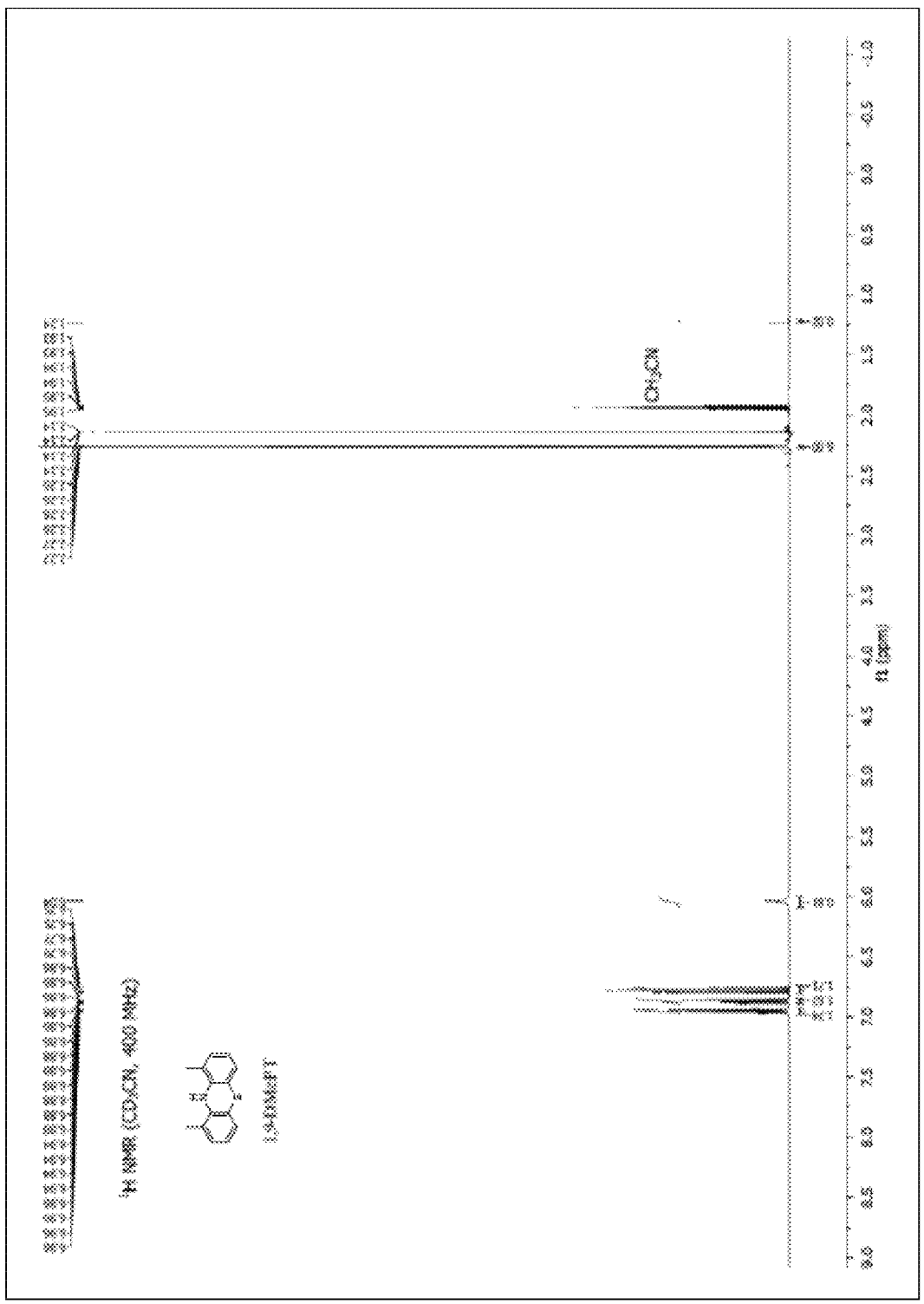
Figure 12C:
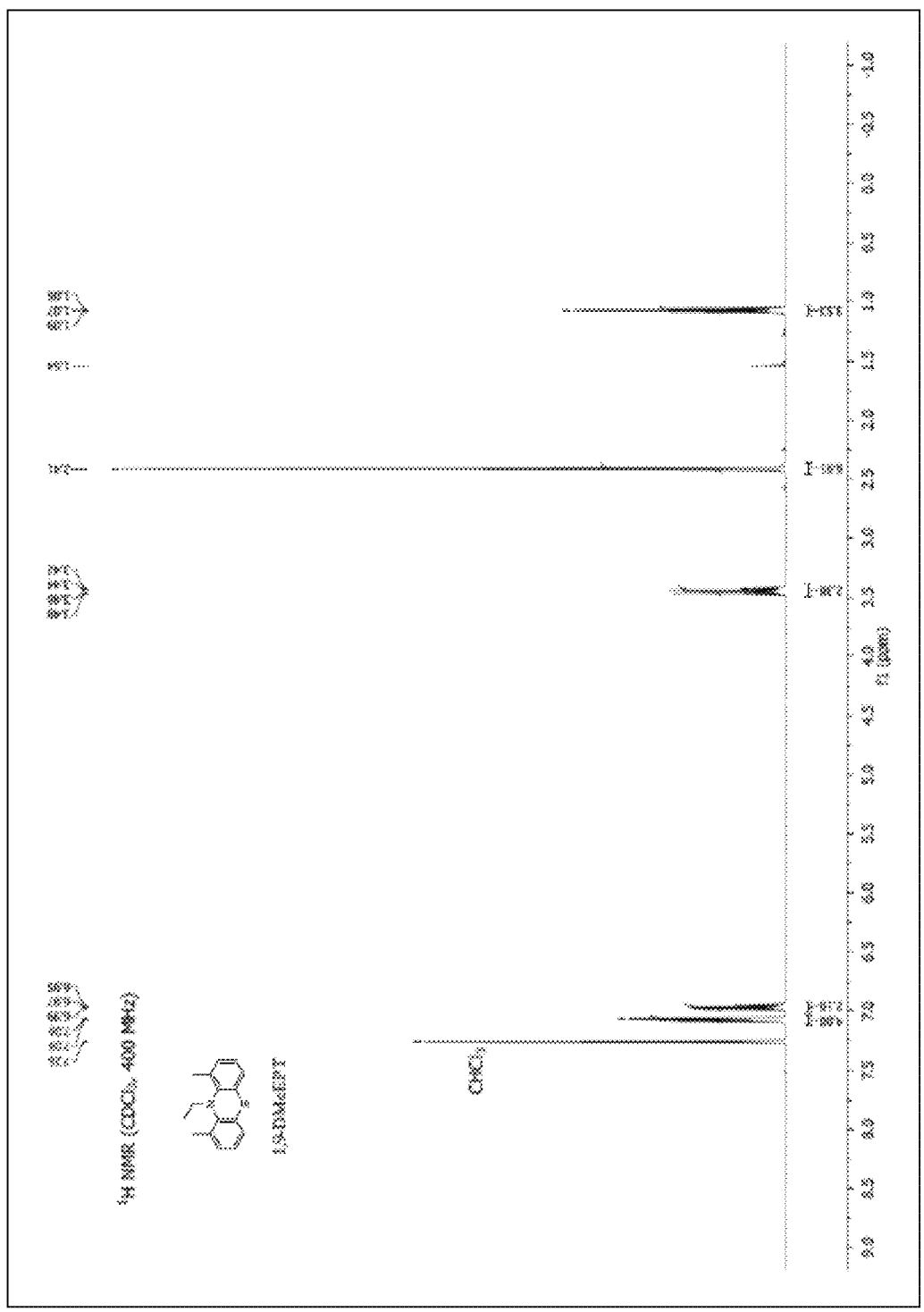
Figure 12D:
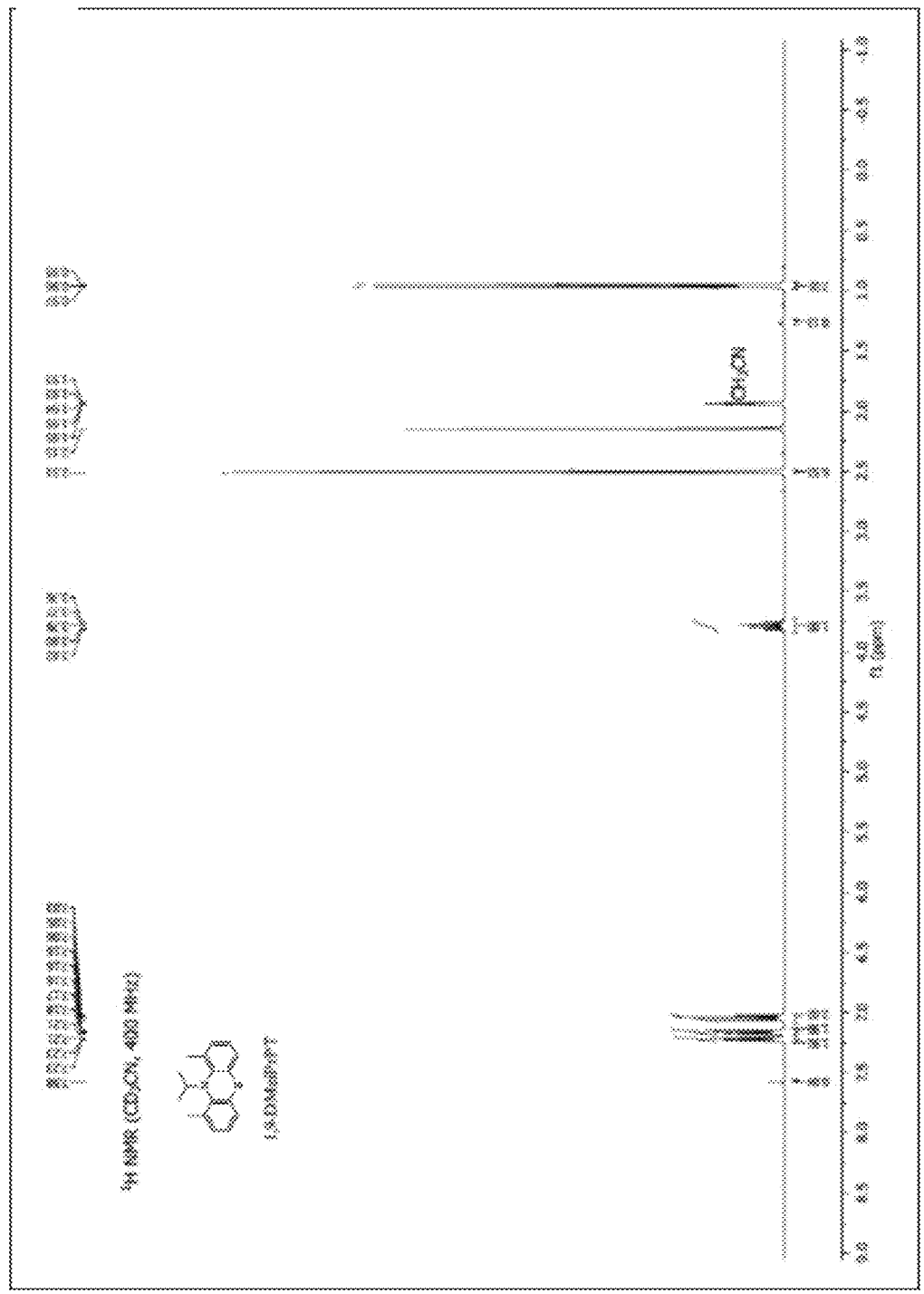
Figure 12E:
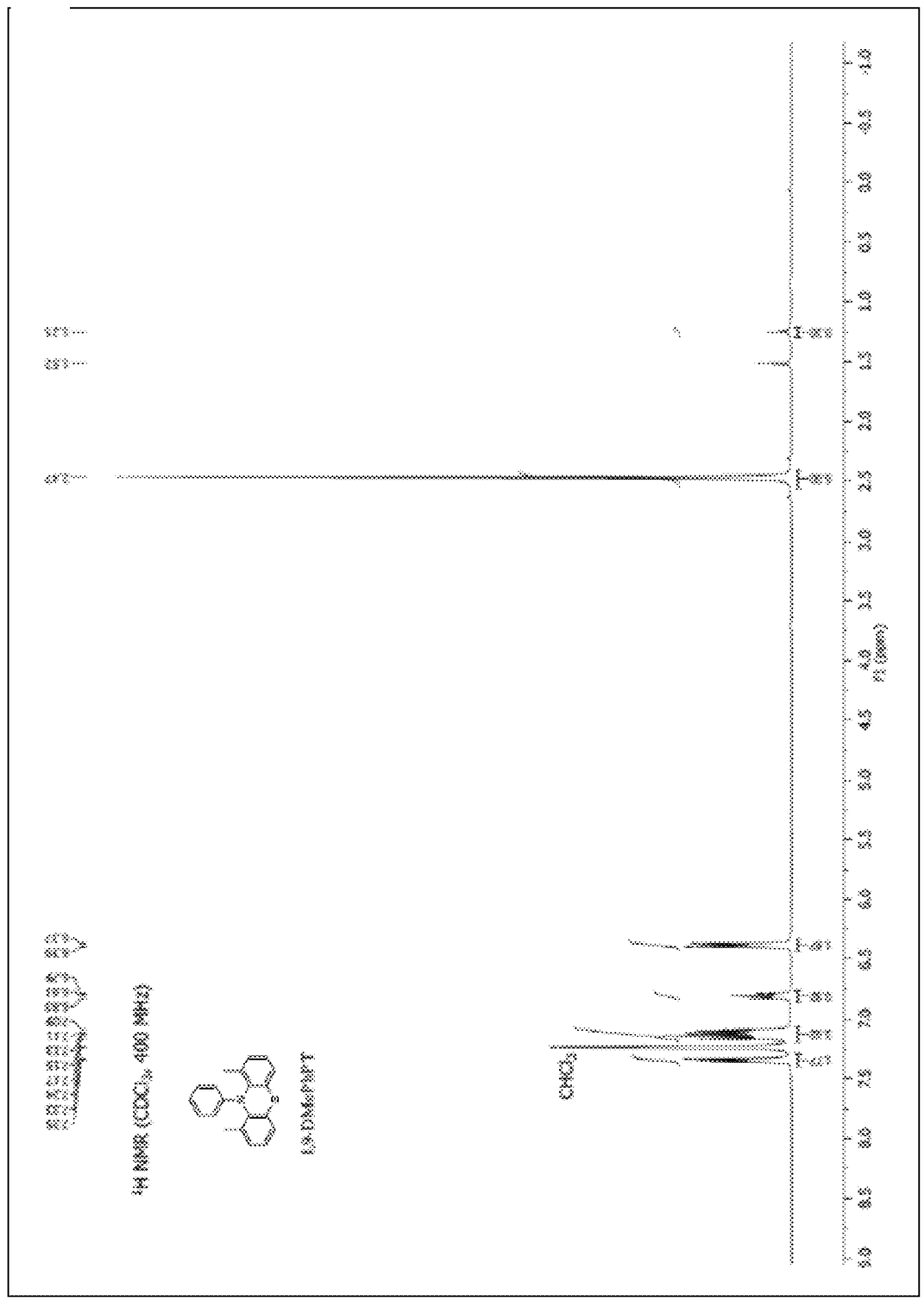

Voltammograms containing the internal reference—either ferrocene or decamethylferrocene—in which the first oxidation event of the phenothiazine derivative was accessed are shown in FIG. 11.

Figure 4:
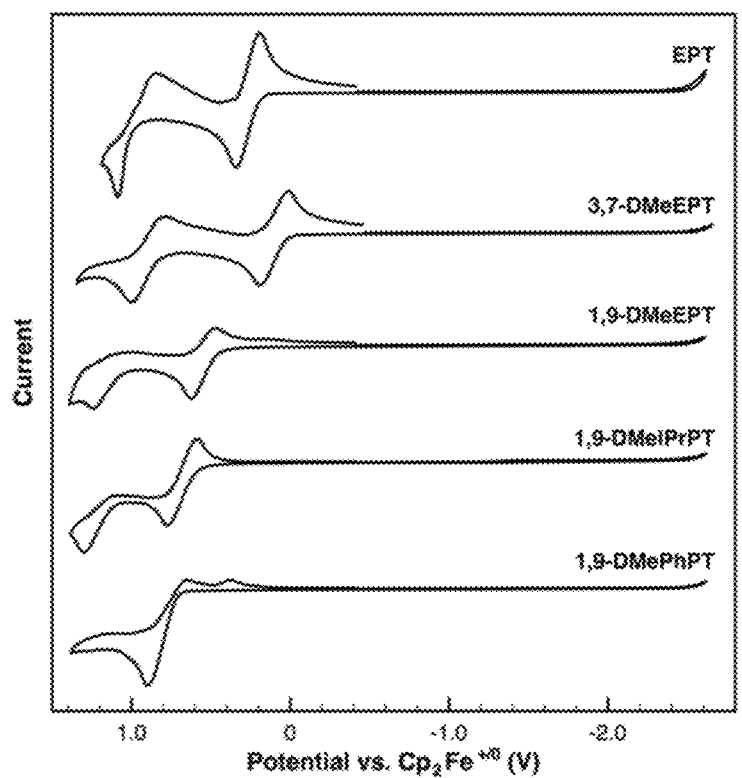
FIG. 4 includes cyclic voltammograms of EPT, 3,7-DMeEPT, 1,9-DMeEPT, 1,9-DMeiPrPT, and 1,9-DMePhPT at 1.6 mM in 0.1 M nBu$_4$NPF$_6$ in DCM vs. Cp$_2$Fe$^{+/0}$ at 0 V, recorded at scan rates of 100 mV/s.

Voltammograms of the phenothiazines (note: no internal reference in these scans) are shown in FIG. 4 in which the full solvent window was scanned.

Example 7

UV-Visible Spectroscopy. UV-vis spectra were obtained using optical glass cuvettes (Starna) with 1 cm path length on an Agilent 8453 diode array spectrophotometer. Spectra of neutral compounds were obtained in DCM at concentrations of 14 µM. Spectra of radical cations were obtained in anhydrous DCM by mixing 0.5 mL of a 0.5 mM solution of TBPASbCl$_6$ in DCM with 2.0 mL of a solution that was 2.5 mM radical cation. The resultant solution contained 0.1 mM radical cation and 1.9 mM neutral analyte. After the cuvette was capped and mixed, UV-vis spectra were recorded immediately.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES 1. a) L. P. Hammett, J. Am. Chem. Soc.1937, 59, 96-103; b) M. J. S. Dewar, P. J. Grisdale, J. Am. Chem. Soc. 1962, 84, 3539-3541; c) M. J. S. Dewar, P. J. Grisdale, J. Am. Chem. Soc. 1962, 84, 3548-3553; d) C. Hansch, A. Leo, R. W. Taft, Chem. Rev. 1991, 91, 165-195; e) K. Bowden, E. J. Grubbs, in *Progress in Physical Organic Chemistry*, John Wiley & Sons, Inc., 2007, pp. 183-224.
2. a) J. H. D. Eland, Int. J. Mass. 1969, 2, 471-484; b) J. P. Maier, D. W. Turner, Faraday Discuss. Chem. Soc. 1972, 54, 149-167; c) L. Andrews, R. T. Arlinghaus, C. K. Payne, I Chem. Soc., Faraday Trans. 2 1983, 79, 885-895; d) J. Cioslowski, S. T. Mixon, J. Am. Chem. Soc. 1992, 114, 4382-4387; e) M. Rubio, M. Merchan, E. Orti, Theor. Chim. Acta 1995, 91, 17-29; f) A. Karpfen, C. H. Choi, M. Kertesz, J. Phys. Chem. A 1997, 101, 7426-7433; g) S. Tsuzuki, T. Uchimaru, K. Matsumura, M. Mikami, K.

Tanabe, *J. Chem. Phys.* 1999, 110, 2858-2861; h) J. C. Sancho-Garcia, A. J. Pérez-Jiménez, *J. Phys. B: At. Mol. Opt. Phys.* 2002, 35, 1509; i) D. Vonlanthen, A. Rudnev, A. Mishchenko, A. Käslin, J. Rotzler, M. Neuburger, T. Wandlowski, M. Mayor, *Chem. Eur. 1* 2011, 17, 7236-7250.

3. a) G. R. Hutchison, M. A. Ratner, T. J. Marks, *J. Am. Chem. Soc.* 2005, 127, 2339-2350; b) S. S. Zade, M. Bendikov, *Chem. Eur. 1* 2007, 13, 3688-3700.
4. R. C. Haddon, *Science* 1993, 261, 1545-1550.
5. Q. Chen, M. T. Trinh, D. W. Paley, M. B. Preefer, H. Zhu, B. S. Fowler, X. Y. Zhu, M. L. Steigerwald, C. Nuckolls, *J. Am. Chem. Soc.* 2015, 137, 12282-12288.
6. a) J. D. Debad, S. K. Lee, X. Qiao, J. Robert A. Pascal, A. J. Bard, *Acta. Chem. Scand.* 1998, 52, 45-50; b) H. M. Duong, M. Bendikov, D. Steiger, Q. Zhang, G. Sonmez, J. Yamada, F. Wudl, *Org. Lett.* 2003, 5, 4433-4436; c) J. Xiao, Y. Divayana, Q. Zhang, H. M. Doung, H. Zhang, F. Boey, X. W. Sun, F. Wudl, *J. Mater. Chem.* 2010, 20, 8167-8170.
7. a) M. D. Casselman, A. P. Kaur, K. A. Narayana, C. F. Elliott, C. Risko, S. A. Odom, *Phys. Chem. Chem. Phys.* 2015, 17, 6905-6912; b) K. A. Narayana, M. D. Casselman, C. F. Elliott, S. Ergun, S. R. Parkin, C. Risko, S. A. Odom, *ChemPhysChem* 2015, 16, 1179-1189.
8. a) J. Chen, C. Buhrmester, J. R. Dahn, *Electrochem. Solid-State Lett.* 2005, 8, A59-A62; b) Z. Chen, Y. Qin, K. Amine, *Electrochim. Acta* 2009, 54, 5605-5613.
9. a) J. R. Dahn, J. Jiang, L. M. Moshurchak, M. D. Fleischauer, C. Buhrmester, L. J. Krause, *J. Electrochem. Soc.* 2005, 152, A1283-A1289; b) L. M. Moshurchak, C. Buhrmester, R. L. Wang, J. R. Dahn, *Electrochim. Acta* 2007, 52, 3779-3784; c) S. Ergun, C. F. Elliott, A. P. Kaur, S. R. Parkin, S. A. Odom, *Chem. Commun.* 2014, 50, 5339-5341; d) A. P. Kaur, S. Ergun, C. F. Elliott, S. A. Odom, *J. Mater. Chem. A* 2014, 2, 18190-18193; e) A. P. Kaur, C. F. Elliott, S. Ergun, S. A. Odom, *J. Electrochem. Soc.* 2015, 163, A1-A7.
10. a) Z. Chen, K. Amine, *Electrochem. Commun.* 2007, 9, 703-707; b) L. M. Moshurchak, W. M. Lamanna, M. Bulinski, R. L. Wang, R. R. Garsuch, J. Jiang, D. Magnuson, M. Triemert, J. R. Dahn, *J. Electrochem. Soc.* 2009, 156, A309-A312; c) L. Zhang, Z. Zhang, H. Wu, K. Amine, *Energy Environ. Sci.* 2011, 4, 2858-2862; d) J. Huang, N. Azimi, L. Cheng, I. A. Shkrob, Z. Xue, J. Zhang, N. L. Dietz Rago, L. A. Curtiss, K. Amine, Z. Zhang, L. Zhang, *J. Mater. Chem. A* 2015, 3, 10710-10714; e) A. P. Kaur, M. D. Casselman, C. F. Elliott, S. R. Parkin, C. Risko, S. A. Odom, *J. Mater. Chem. A* 2016, 4, 5410-5414.
11. S. S. C. Chu, D. Van der Helm, *Acta Cryst. Sect. B* 1974, 30, 2489-2490.
12. S. Ergun, M. D. Casselman, A. P. Kaur, S. R. Parkin, S. A. Odom, *manuscript submitted to RSC Adv.*
13. S. Ergun, C. F. Elliott, A. P. Kaur, S. R. Parkin, S. A. Odom, *J. Phys. Chem. C* 2014, 118, 14824-14832.
14. T. Koopmans, *Physica* 1934, 1, 104-113.
15. J. F. Janak, *Phys. Rev. B* 1978, 18, 7165-7168.
16. Odom, S. A.; Ergun, S.; Poudel, P. P.; Parkin, S. R. *Energy Environ. Sci.* 2014, 7, 760-767.
17. Ergun, S.; Elliott, C. F.; Kaur, A. P.; Parkin, S. R.; Odom, S. A. *Chem. Commun.* 2014, 50, 5339-5341.
18. Artamkina, G. A.; Sergeev, A. G.; Stern, M. M.; Beletskaya, I. P. *Synlett* 2006, 235-238.
19. Hurt, C. R.; Lingappa, V.; Freeman, B.; Atuegbu, A.; Kitaygorodskyy, A. Phenothiazinium compounds as antiviral agents and their preparation. U.S. Pat. No. 8,809, 317B2, 2014.
20. Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery Jr., J. A.; Peralta, J. E.; Ogliaro, F.; Bearpark, M. J.; Heyd, J.; Brothers, E. N.; Kudin, K. N.; Staroverov, V. N.; Kobayashi, R.; Normand, J.; Raghavachari, K.; Rendell, A. P.; Burant, J. C.; Iyengar, S. S.; Tomasi, J.; Cossi, M.; Rega, N.; Millam, N. J.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, O.; Foresman, J. B.; Ortiz, J. V.; Cioslowski, J.; Fox, D. J. *Gaussian* 09, Gaussian, Inc.: Wallingford, Conn., USA, 2009.
21. Becke, A. D. *J. Chem. Phys.* 1993, 98, 5648-5652.
22. Lee, C.; Yang, W.; Parr, R. G. *Phys. Rev. B* 1988, 37, 785-789.
23. Otwinowski, Z. & Minor, W. (1997) *Methods in Enzymology* 276 part A, 307-326. C. W. Carter, Jr. & R. M. Swet, Eds., Academic Press.
24. Bruker-AXS (2006). *APEX2* Bruker-AXS Inc., Madison, Wis., USA.
25. Krause, L., Herbst-Irmer, R., Sheldrick, G. M. & Stalke, D. *J. Appl. Cryst.* 2015, 48, 3-10.
26. Sheldrick, G. M. *Acta Cryst.* 2015, A71, 3-8.
27. Sheldrick, G. M. *Acta Cryst.* 2015, C71, 3-8.
28. *International Tables for Crystallography*, vol C: A. J. C. Wilson, Ed. (1992). Kluwer Academic Publishers, Holland.

It will be understood that various details of the presently disclosed subject matter can be changed without departing from the scope of the subject matter disclosed herein. Furthermore, the foregoing description is for the purpose of illustration only, and not for the purpose of limitation.

We claim:
1. A compound according to the formula:

wherein
$R_1$ and $R_9$ are independently selected from the group consisting of H, alkyl, aryl, perfluoroaryl, perfluoroalkyl, alkylaryl, alkoxyaryl, alkylcarboxyl, aryl carbonyl, haloalkyl, perfluoroalkyl, glycols, haloaryl, a negative electrolyte, and a polymer, so long as when $R_1$ is H, $R_9$ is not H;
$R_3$ and $R_7$ are independently selected from the group consisting of H, alkyl, perfluoroalkyl, alkylaryl, alkoxyaryl, alkylcarboxyl, aryl carbonyl, haloalkyl, perfluoroalkyl, glycols, haloaryl, a negative electrolyte, and a polymer; and $R_{10}$ is selected from the group consisting of aryl, alkylaryl, alkoxyaryl, aryl carbonyl perfluoroaryl, glycols, haloaryl, an oligomer, and a polymer.

2. The compound according to claim 1, selected from the group consisting of:

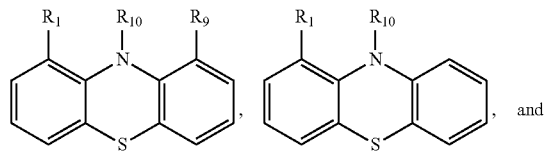

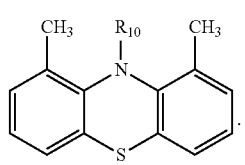

3. The compound according to claim 1, wherein $R_{10}$ is aryl.

4. The compound according to claim 1, wherein $R_{10}$ is phenyl.

5. A compound according to the formula:

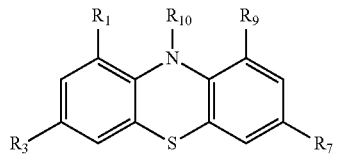

wherein $R_1$ and $R_9$ are each $CH_3$ or $CF_3$, $R_3$ and $R_7$ are independently selected from the group consisting of H, alkyl, perfluoroalkyl, alkylaryl, alkoxyaryl, alkylcarboxyl, aryl carbonyl, haloalkyl, perfluoroalkyl, glycols, haloaryl, a negative electrolyte, and a polymer; and $R_{10}$ is selected from the group consisting of aryl, alkylaryl, alkoxyaryl, aryl carbonyl, perfluoroaryl, haloaryl, an oligomer, and a polymer;

a compound selected from the group consisting of:

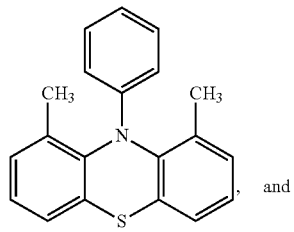 [SMILES: Cc1cccc2c1N(c1ccccc1)c1c(C)cccc1S2]

or a compound according to the formula:

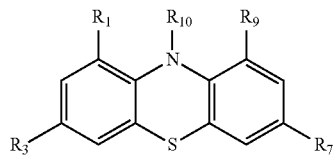

wherein $R_1$ and $R_9$ are independently selected from the group consisting of alkyl, aryl, perfluoroaryl, perfluoroalkyl, alkylaryl, alkoxyaryl, alkylcarboxyl, aryl carbonyl, haloalkyl, perfluoroalkyl, glycols, haloaryl, a negative electrolyte, and a polymer;

$R_3$ and $R_7$ are independently selected from the group consisting of H, alkyl, perfluoroalkyl, alkylaryl, alkoxyaryl, alkylcarboxyl, aryl carbonyl, haloalkyl, perfluoroalkyl, glycols, haloaryl, a negative electrolyte, and a polymer; and $R_{10}$ is selected from the group consisting of aryl, alkylaryl, alkoxyaryl, aryl carbonyl, perfluoroaryl, haloaryl, an oligomer, and a polymer.

6. A rechargeable battery comprising:
a negative electrode;
a positive electrode; and
an electrolyte comprising the compound of claim 5.

7. The battery of claim 6, wherein the positive electrode is immersed in the electrolyte.

8. The battery of claim 6, wherein the electrolyte further comprises a charge-carrying medium and a lithium salt.

9. The battery of claim 6, wherein the positive electrode comprises a high-voltage cathode.

10. The battery of claim 9, wherein the high-voltage cathode is selected from LiFePO$_4$ (LFP), LiMn$_2$O$_4$ (LMO), LiCoO$_2$ (LCO), LiNi$_{1/3}$Mn$_{1/3}$Co$_{1/3}$O$_2$ (NMC), and LiNi$_{0.8}$Co$_{0.15}$Al$_{0.05}$O$_2$ (NCA).

11. The battery of claim 10, wherein the negative electrode is a graphitic anode.

12. A rechargeable battery comprising:
a negative electrode;
a positive electrode;
an electrolyte comprising a charge-carrying medium; and
a redox shuttle comprising the compound of claim 5.

13. A battery comprising a passivating electrolyte additive, wherein the passivating electrolyte additive comprises the compound of claim 5.

14. The battery of claim 13, wherein the battery is selected from the group consisting of a lithium-ion battery, a lithium-air battery, and a sodium-ion battery.

15. A battery comprising a photopolymerization initiator or photoredox catalyst, wherein the photopolymerization initiator or photoredox catalyst comprises the compound of claim 5.

16. A battery comprising an electrode material, wherein the electrode material comprises the compound of claim 5.

17. The battery of claim 16, wherein the battery is a non-aqueous redox flow battery.

18. An array comprising two or more of the battery of claim 6.

19. The array of claim 18, wherein the two or more battery are connected in a series.

20. A rechargeable battery comprising:
a negative electrode;
a positive electrode; and
an electrolyte comprising the compound of claim 1.

21. A rechargeable battery comprising:
a negative electrode;
a positive electrode;
an electrolyte comprising a charge-carrying medium; and
a redox shuttle comprising the compound of claim 1.

* * * * *